US005736534A

United States Patent [19]
Arnold

[11] Patent Number: 5,736,534
[45] Date of Patent: Apr. 7, 1998

[54] 4-HETEROCYCLYL-SUBSTITUTED QUINAZOLINE DERIVATIVES, PROCESSES FOR THEIR PREPARATION AND THEIR USE AS ANTI-CANCER AGENTS

[75] Inventor: Lee D. Arnold, Westborough, Mass.

[73] Assignee: Pfizer Inc., New York, N.Y.

[21] Appl. No.: 682,565

[22] PCT Filed: Jan. 27, 1995

[86] PCT No.: PCT/IB95/00061

§ 371 Date: Jul. 29, 1996

§ 102(e) Date: Jul. 29, 1996

[87] PCT Pub. No.: WO95/23141

PCT Pub. Date: Aug. 31, 1995

Related U.S. Application Data

[63] Continuation-in-part of Ser. No. 200,259, Feb. 23, 1994, abandoned.

[51] Int. Cl.$^6$ .................. C07D 403/02; C07D 402/14; A61K 31/535; A61K 31/54
[52] U.S. Cl. .................. 514/63; 514/213; 514/234.5; 514/259; 514/260; 540/594; 544/116; 544/284; 544/293
[58] Field of Search .................. 544/284, 293, 544/116; 514/259, 260, 63, 213, 234.5; 540/594

[56] References Cited

U.S. PATENT DOCUMENTS

| | | | |
|---|---|---|---|
| 3,884,919 | 5/1975 | Birchall et al. | 514/259 |
| 4,012,513 | 3/1977 | Birchall et al. | 514/259 |
| 5,475,001 | 12/1995 | Barker | 514/258 |
| 5,576,322 | 11/1996 | Takase et al. | 514/260 |
| 5,580,870 | 12/1996 | Barker et al. | 514/234.5 |

FOREIGN PATENT DOCUMENTS

| | | |
|---|---|---|
| 520 722 | 12/1992 | European Pat. Off. . |
| 566 226 | 10/1993 | European Pat. Off. . |
| 602 851 | 6/1994 | European Pat. Off. . |
| 635 498 | 1/1995 | European Pat. Off. . |
| WO 92/20642 | 11/1992 | WIPO . |

OTHER PUBLICATIONS

Goodale et al., Journal of the American Chemical Society, vol. 71, 1893 (May 1949).

*Primary Examiner*—Matthew V. Grumbling
*Attorney, Agent, or Firm*—Peter C. Richardson; Gregg C. Benson; A. Dean Olson

[57] ABSTRACT

This invention relates to certain 4-aminoquinazolines and the pharmaceutically acceptable salts and stereoisomers thereof, the formula whereof are described herein. The compounds are useful for the treatment of hyperproliferative diseases, particularly as anti-cancer agents.

20 Claims, No Drawings

4-HETEROCYCLYL-SUBSTITUTED QUINAZOLINE DERIVATIVES, PROCESSES FOR THEIR PREPARATION AND THEIR USE AS ANTI-CANCER AGENTS

This application was filed under 35 U.S.C. §371 based on PCT/IB95/00061, which was filed on Jan. 27, 1995 which was a continuation-in-part of U.S. application Ser. No. 08/200,259 which was filed on Feb. 23, 1994 and is now abandoned.

BACKGROUND OF THE INVENTION

This invention relates to quinazoline derivatives and methods of using the same, particularly as anti-cancer agents, in mammals.

Many of the current treatment regimes for cancer utilize compounds which inhibit DNA synthesis. Such compounds are toxic to cells generally but their toxic effect on the rapidly dividing tumor cells can be beneficial. Alternative approaches to anti-cancer agents which act by mechanisms other than the direct inhibition of DNA synthesis have been explored in order to enhance the selectivity of action against cancer cells.

It is known that a cell may become cancerous by virtue of the transformation of a portion of its DNA into an oncogene (i.e. a gene which, on activation, leads to the formation of malignant tumor cells). Many oncogenes encode proteins which are aberrant tyrosine kinases capable of causing cell transformation. Alternatively, the overexpression of a normal proto-oncogenic tyrosine kinase may also result in proliferative disorders, sometimes resulting in a malignant phenotype.

Receptor tyrosine kinases are large enzymes which span the cell membrane and possess an extracellular binding domain for growth factors such as epidermal growth factor, a transmembrane domain, and an intracellular portion which functions as a kinase to phosphorylate specific tyrosine residues in proteins and hence to influence cell proliferation. It is known that such kinases are frequently aberrantly expressed in common human cancers such as breast cancer, gastrointestinal cancer such as colon, rectal or stomach cancer, leukemia, and ovarian, bronchial or pancreatic cancer. It has also been shown that epidermal growth factor receptor (EGFR) which possesses tyrosins kinase activity is mutated and/or overexpressed in many human cancers such as brain, lung, squamous cell, bladder, gastric, breast, head and neck, oesophageal, gynecological and thyroid tumors.

Accordingly, it has been recognized that inhibitors of receptor tyrosine kinases are useful as a selective inhibitors of the growth of mammalian cancer cells, For example, erbstatin, a tyrosine kinase inhibitor selectively attenuates the growth in athymic nude mice of a transplanted human mammary carcinoma which expresses epidermal growth factor receptor tyrosine kinase (EGFR) but is without effect on the growth of another carcinoma which does not express the EGF receptor.

Various other compounds, such as styrene derivatives, have also been shown to possess tyrosine kinase inhibitory properties. More recently three European patent publications, namely EP 0 566 226 A1, EP 0 602 851 A1 and EP 0 520 722 A1 have disclosed that certain quinazoline derivatives possess anti-cancer properties which result from their tyrosine kinase inhibitory properties. Also PCT publication WO 92/20642 discloses bis-mono and bicyclic aryl and heteroaryl compounds as tyrosine kinase inhibitors.

In addition U.S. Pat. No. 4,012,513 discloses certain 1-(heterocyclic)-indol-3-yl-acetic acid derivatives that have anti-inflammatory, analgesic and antipyretic activity.

Although the anti-cancer compounds described above make a significant contribution to the art there is a continuing search in this field of art for improved anti-cancer pharmaceuticals.

SUMMARY OF THE INVENTION

This invention is directed to quinazoline derivatives, particularly 4-aminoquinazolines, that are useful as anti-cancer agents. The compounds of this invention have the Formula I

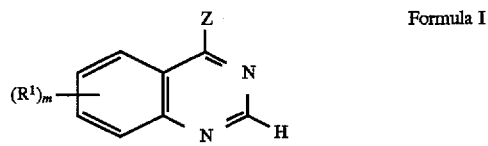

Formula I and the pharmaceutically acceptable salts and stereoisomers thereof wherein either A, B or C Z is

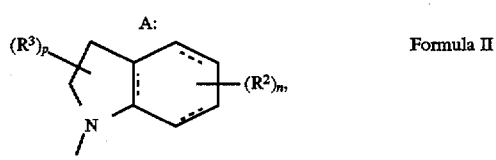

Formula II

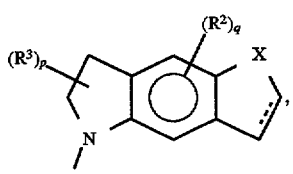

Formula III

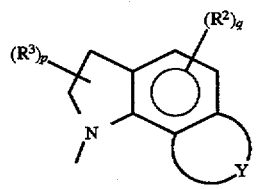

Formula IV or

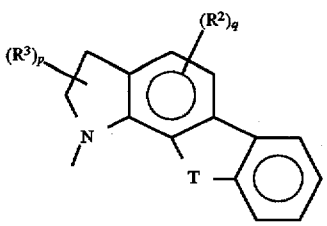

Formula V wherein

X is methylene, thio, —N(H)— or oxy;

Y completes a 5 or 6 membered aromatic, or partially saturated ring which may incorporate an oxygen or sulfur atom;

T is methylene, —N(H)—, thio or oxy;

Z is

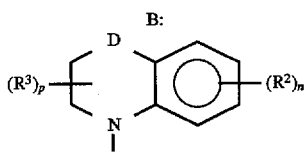
Formula VI wherein D may be saturated carbon, oxy or thio; or
Z is

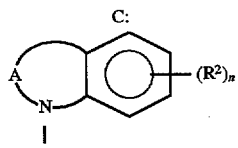
Formula VIII wherein A completes a 7 to 9 membered mono-unsaturated mono-aza ring;

$R^1$ for each occurrence is independently a. trifluoromethyl, halo, nitro, hydroxy, amino, cyano, $(C_1-C_4)$alkyl, $(C_1-C_4)$alkoxy, $(C_1-C_4)$alkoxycarbonyl, $(C_1-C_4)$alkanoyloxy, $(C_1-C_4)$alkanoylamino, carboxy, phenoxy, benzoyloxy, carbamoyl, mono-N- or di-N-N-di-$(C_1-C_4)$alkylcarbamoyl, mono-N- or di-N,N-$(C_1-C_4)$alkylamino, mono-N or di-N,N-(hydroxy$(C_2-C_4)$alkyl)amino, mono-N or di-N,N-(($C_1-C_4$)alkoxy$(C_2-C_4)$alkyl)amino, anilino, pyrrolidin-1-yl, piperidin-1-yl, morpholino, piperazin-1-yl, 4-$(C_1-C_4)$alkylpiperazin-1-yl, $(C_1-C_4)$alkylthio, phenylthio, or such groups substituted on $(C_1-C_4)$alkyl;

b. hydroxy$(C_2-C_4)$alkoxy$(C_1-C_4)$alkyl, $(C_1-C_4)$alkoxy-$(C_2-C_4)$alkoxy-$(C_1-C_4)$alkyl, hydroxy $(C_2-C_4)$alkylthio$(C_1-C_4)$alkyl, $(C_1-C_4)$alkoxy $(C_2-C_4)$alkylthio$(C_1-C_4)$alkyl, hydroxyamino, benzoylamino, mono-N or di-N,N-$(C_1-C_4)$ alkylcarbamoylmethylamino, carbamoylmethylamino, $(C_1-C_4)$ alkoxycarbonylamino, $(C_1-C_4)$alkanoylamino, carboxymethylamino, $(C_1-C_4)$ alkoxycarbonylmethylamino, $(C_1-C_4)$alkoxyamino, $(C_2-C_4)$alkanoyloxyamino, phenyl$(C_1-C_4)$ alkylamino, $(C_1-C_4)$alkylsulphonylamino, benzenesulphonamido, 3-phenylureido, 2-oxopyrrolidin-1-yl, 2,5-dioxopyrrolidin-1-yl, ureido, $(C_1-C_4)$alkoxy$(C_1-C_4)$alkylcarbonylamino, $(C_1-C_4)$alkylsulfinyl, $(C_1-C_4)$alkylsulfonyl, $(C_1-C_4$ $alkoxy(C_2C_4))$alkylthio, mono-, di-or trifluoromethyloxy, $(C_1-C_4)$alkylenedioxy, benzyloxy, azido, guanidino, aminocarbonyl, mono-N- or di-N,N-$(C_1-C_4)$alkylaminocarbonyl, phenyl $(C_1-C_4)$alkoxy, carboxymethoxy, $(C_1-C_4,)$ alkoxycarbonylmethoxy, carbamoylmethoxy, mono-N or di-N,N-$(C_1-C_4)$alkyl carbamoylmethoxy, mono-N- or di-N,N-(hydroxy $(C_2-C_4)$alkyl)carboxamido, mono-N- or di-N,N-( $(C_1-C_4)$alkoxy $(C_2-C_4)$alkyl)carboxamido or bis( $(C_1-C_4)$alkanesulfonyl)amido; or c. $(C_2-C_4)$alkoxy, $(C_2-C)$alkylthio, $(C_2-C_4)$ alkanoyloxy, $(C_2-C_4)$alkylamino, $(C_1-C_4)$alkyl $(C_1-C_4)$alkylanedioxy, or $(C_2-C_4)$alkanoylamino; each such group substituted with amino, halo, hydroxy, $(C_2-C_4)$alkanoyloxy $(C_1-C_4)$alkoxy, mono-N-or di-N,N-$(C_1-C_4)$alkylamino, mono-N or di-N,N-(hydroxy$(C_2-C_4)$alkyl)amino, mono-N or di-N,N-(($C_1-C_4$)alkoxy$(C_2-C_4)$alkyl)amino, $(C_1-C_4)$alkanoylamino, phenoxy, anilino, imidazol-1-yl, phenylthio, piperidino, morpholino, piperazin-1-yl-,4-$(C_1-C_4)$alkylpiperazin-1-yl-, carboxy, $(C_1-C_4)$alkoxycarbonyl, carbamoyl, mono-N- or di-N,N-$(C_1-C_4)$alkylcarbamoyl, carboxamido, mono-N- or di-N,N-$(C_1-C_4)$alkylcarboxamido or mono-N- or di-N,N(hydroxy$(C_2-C_4)$alkyl) carboxamido;

wherein any phenyl in a $R^1$ substituent is optionally mono- or di- substituted with halo, nitro, trifluoromethyl, hydroxy, $(C_1-C_4)$alkoxy or $(C_1-C_4)$ alkyl and said $(C_1-C_4)$alkylenedioxy is linked at both ends to the quinazoline moiety;

$R^2$ for each occurrence is independently mono-, di- or tri-fluoromethyl, halo, nitro, hydroxy, amino, azido, isothiocyano, $(C_1-C_4)$alkyl, phenyl, thienyl, $(C_1-C_4)$ alkoxy, benzyloxy, phenoxy, $(C_2-C_6)$alkenyl, $(C_1-C_6)$ alkynyl, $(C_1-C_4)$alkylenedioxy, cyano, benzoylamino, trifluoromethylcarbonylamino, $(C_1-C_4)$alkanoylamino, $(C_1-C_4)$alkanoyl, N-mono- or N,N-di-$(C_1-C_4)$ alkylamino, $(C_1-C_4)$alkylsulfonylamino, trifluoromethylsulfonylamino, $(C_1-C_4)$alkylthio, $(C_1-C_4)$alkylsulfinyl or $(C_1-C_4)$alkylsulfonyl, pyrrol-1-yl, piperidin-1-yl or pyrrolidin-1-yl, said phenyl, benzyloxy, phenoxy and benzoylamino optionally mono-substituted with halo, nitro, trifluoromethyl, hydroxy or $(C_1-C_4)$alkyl and said $(C_1-C_4)$ alkylenedioxy is linked at both ends to adjacent carbons on the benzene moiety;

$R^3$ for each occurrence is independently hydroxy, amino, N-mono- or N,N-di-$(C_1-C_4)$alkylamino, sulfo, or $(C_1-C_4)$alkoxy (provided that such groups are not attached to a ring carbon which is adjacent to an oxy, thio or —N—), or $R^3$ for each occurrence is independently carboxy, hydroxy$(C_1-C_4)$alkyl, $(C_1-C_4)$alkoxy $(C_1-C_4)$alkyl, amino$(C_1-C_4)$alkyl, mono-N- or di-N,N-$(C_1-C_4)$alkylamino$(C_1-C_4)$alkyl, morpholino $(C_1-C_4)$ alkyl, 4(C $_1-C_4$)alkyl-piperazin-1-yl$(C_1-C_4)$alkyl, carboxy$(C_1-C_4)$alkyl, $(C_1-C_4)$alkoxycarbonyl, sulfo $(C_1-C_4)$alkyl or $(C_1-C_4)$alkyl;

where m is 0-3;

n is 0-4;

is 0, 1 or 2; and q is 0, 1 or 2;

with the proviso that 4-(3,4-dihydro-2H-quinolin-1-yl)-quinazoline is not included.

A first group of preferred compounds of Formula I consists of those compounds wherein Z is

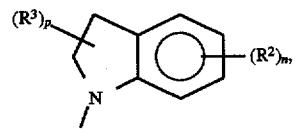

-continued

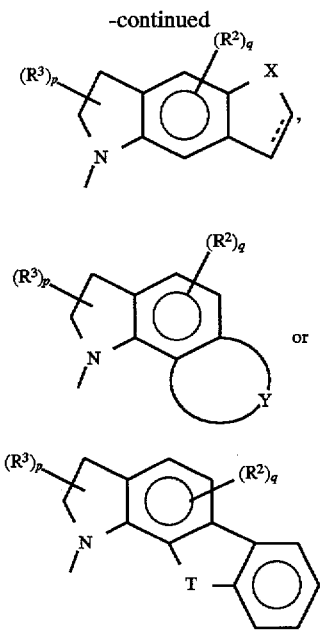

$R^1$ for each occurrence is independently hydroxy, $(C_1-C_4)$ alkoxy, hydroxy$(C_2-C_2)$alkoxy, amino$(C_2-C_4)$alkyl, amino$(C_2-C_4)$alkoxy, $(C_1-C_4)$alkoxy$(C_2-C_4)$alkoxy, $(C_1-C_4)$alkylenedioxy, hydroxy$(C_1-C_4)$alkyl$(C_1-C_4)$ alkylenedioxy, $(C_1-C_4)$alkoxy$(C_1-C_4)$alkyl$(C_1-C_4)$ alkylenedioxy, mono-N- or di-N,N-$(C_1-C_4)$alkylamino $(C_2-C_4)$alkoxy, 3- or 4-$(C_1-C_4)$alkoxy-(2-hydroxy)- $(C_3-C_4)$alkoxy, carboxy$(C_1-C_4)$alkoxy, morpholino $(C_2-C_4)$alkoxy, imidazol-1-yl$(C_2-C_4)$alkoxy, 4$(C_1-C_4)$ alkylpiperazin-1-yl-$(C_2-C_4)$alkoxy, $(C_1-C_4)$alkoxy $(C_1-C_4)$alkanoyloxy, nitro, hydroxylamino, amino, mono-N- or di-N,N-$(C_1-C_4)$alkylamino, $(C_1-C_4)$ alkanoylamino, hydroxy$(C_2-C_4)$alkylamino, $(C_1-C_4)$ alkoxy$(C_2-C_4)$alkylamino, $(C_1-C_4)$alkylsulfonamino, morpholino, $(C_1-C_4)$alkyl-piperazin-1-yl, bis$(C_1-C_4)$ alkanesulfonamido, di$(C_1-C_4)$alkylamino$(C_2-C_4)$ alkylamino, $(C_1-C_4)$alkylamino$(C_2-C_4)$alkylamino, imidazol-1-yl, piperidin-1-yl, pyrrolidin-1-yl, $(C_1-C_4)$ alkoxy$(C_1-C_4)$alkylcarbonylamino, N-$(C_1-C_4)$alkyl-N-$(C_1-C_4)$alkanoyl-amino, carboxy, $(C_1-C_4)$ alkoxycarbonyl, $(C_1-C_4)$alkoxycarbonyl$(C_1-C_4)$ alkoxy, amido, mono-N- or di-N,N-$(C_1-C_4)$ alkylaminocarbonyl, mono-N- or di-N,N-(hydroxy $(C_2-C_4)$alkyl)aminocarbonyl, $(C_1-C_4)$alkyl, hydroxy $(C_1-C_4)$alkyl, mono-N- or di-N,N-(($C_1-C_4)$alkoxy $(C_1-C_4)$alkyl)amino$(C_1-C_4)$alkyl, mono-N- or di-N,N-$(C_1-C_4)$alkylamino$(C_1-C_4)$alkyl, $(C_1-C_4)$ alkanoylamino$(C_1-C_4)$alkyl, $(C_1-C_4)$alkoxy$(C_2-C_4)$ alkoxy$(C_1-C_4)$alkyl, $(C_1-C_4)$alkylthio, $(C_1-C_4)$alkoxy $(C_2-C_4)$alkylthio or hydroxy$(C_2-C_4)$alkylthio;

$R^2$ for each occurrence is independently nitro, halo, $(C_1-C_4)$alkyl, pyrrol-1-yl, hydroxyl, amino, mono-N- or di-N,N-$(C_1-C_4)$alkylamino, amino$(C_1-C_4)$alkyl, azido, ethenyl, ethynyl, $(C_1-C_4)$alkylenedioxy, phenyl or $(C_1-C_4)$alkylthio;

$R^3$ for each occurrence is independently hydroxy$(C_1-C_4)$ alkyl, $(C_1-C_4)$alkyl, amino$(C_1-C_4)$alkyl, carboxy $(C_1-C_4)$alkyl or mono-N- or di-N,N-$(C_1-C_4)$ alkylamino$(C_1-C_4)$alkyl;

m is 0, 1 or 2;

p is 0 or 1; and n is 0, 1, 2, or 3.

Within this first group of preferred compounds of Formula I are a first group of especially preferred compounds wherein Z is

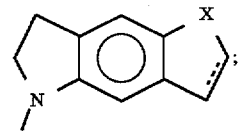

X is —N(H)—; and $R^1$ for each occurrence is substituted independently in the 6 and/or 7 position.

A second group of especially preferred compounds within the above first group of preferred compounds of Formula I are compounds wherein Z is

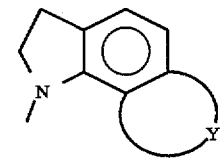

or

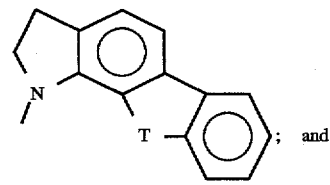

$R^1$ for each occurrence is substituted in the 6 and/or 7 position.

A third group of especially preferred compounds within the above first group of preferred compounds of Formula I are compounds wherein Z is

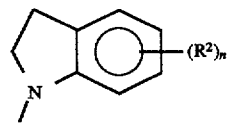

n is 1, 2 or 3;

m is 1 or 2;

$R^1$ for each occurrence is substituted independently in the 6 and/or 7 positions and is $(C_1-C_4)$alkyl, $(C_1-C_4)$ alkoxy, hydroxy$(C_2-C_4)$alkoxy, $(C_1-C_4)$alkoxy $(C_2-C_4)$alkoxy, carboxy$(C_1-C_4)$alkoxy, $(C_1-C_4)$ alkoxycarbonyl$(C_1-C_4)$alkoxy, imidazol-1-yl-$(C_2-C_4)$ alkoxy, morpholino$(C_2-C_4)$alkoxy, 4-$(C_1-C_4)$ alkylpiperazin-1-yl-$(C_1-C_4)$alkoxy, $(C_1-C_4)$alkoxy-2-hydroxy$(C_3-C_4)$alkoxy, amino, $(C_1-C_4)$alkylamino, di-N,N-alkylamino, $(C_1-C_4)$alkanoylamino, $(C_1-C_4)$ alkylsulfonylamido, morpholino, $(C_1-C_4)$ alkylpiperazin-1-yl, mono-N- or di-N,N-$(C_1-C_4)$ alkylamino$(C_2-C_4)$alkylamino; and $R^2$ for each occurrence is independently 4-hydroxy, 4-amino, 5-fluoro, 5-hydroxy, 5-amino, 6-halo, 6-methyl, 6-ethenyl, 6-ethynyl, 6-nitro or 7-methyl.

Particularly preferred compounds within the above group of especially preferred compounds are compounds wherein $R^2$ for each occurrence is independently halo, nitro, hydroxy or methyl;
$R^1$ is $(C_1-C_4)$alkoxy or $(C_1-C_4)$alkyl;
m is 2; and
n is 1 or 2.

Other particularly preferred compounds within the above group of especially preferred compounds are compounds wherein a. m is 2;
   $R^1$ is 6-methoxy;
   $R^1$ is 7-methoxy;
   n is 2;
   $R^2$ is 5-fluoro; and
   $R^2$ is 6-bromo;
b. m is 2;
   $R^1$ is 6-(2-methoxyethoxy);
   $R^1$ is 7-(2-methoxyethoxy);
   n is 1; and
   $R^2$ is 6-chloro;
c. m is 2;
   $R^1$ is 6-methoxy;
   $R^1$ is 7-(2-hydroxyethoxy);
   n is 1; and
   $R^2$ is 6-chloro;
d. m is 1;
   $R^1$ is 6-amino;
   n is 1; and
   $R^2$ is 6-chloro;
e. m is 2;
   $R^1$ is 6-methoxy;
   $R^1$ is 7-(3-hydroxypropoxy);
   n is 1; and
   $R^2$ is 6-chloro;
f. m is 2;
   $R^1$ is 7-(2-imidazol-1-yl-ethoxy);
   $R^1$ is 6-methoxy;
   n is 1; and
   $R^2$ is 6-chloro;
g. m is 2;
   $R^1$ is 6-methoxy;
   $R^1$ is 7-methoxy;
   n is 1; and
   $R^2$ is 5-amino;
h. m is 2;
   $R^1$ is 6-methoxy;
   $R^1$ is 7-(2-methoxy-ethoxy);
   n is 2;
   $R^2$ is 5-fluoro; and
   $R^2$ is 6-bromo;
i. m is 2;
   $R^1$ is 6-methoxy;
   $R^1$ is 7-methoxy;
   n is 2;
   $R^2$ is 5-amino; and
   $R^2$ is 6-chloro;
or
j. m is 2;
   $R^1$ is 6-methoxy;
   $R^1$ is 7-(2-hydroxy-3-methoxy)propoxy;
   n is 1; and
   $R^2$ is 6-chloro.

A second group of preferred compounds of Formula I are those compounds wherein

Z is

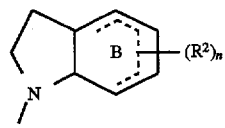

the B six membered ring has 0, 1 or 2 double bonds in the dotted line region;
n is 0–2;
$R^2$ for each occurrence is independently halo, hydroxy or $(C_1-C_4)$alkyl;
m is 0, 1 or 2; and
$R^1$ for each occurrence is substituted independently in the 6 and/or 7 positions and is hydroxy, $(C_1-C_4)$alkoxy, hydroxy$(C_2-C_4)$alkoxy, amino$(C_2-C_4)$alkyl, amino$(C_2-C_4)$alkoxy, $(C_1-C_4)$alkoxy$(C_2-C_4)$alkoxy, $(C_1-C_4)$alkylenedioxy, hydroxy$(C_1-C_4)$alkyl$(C_1-C_4)$alkylenedioxy, $(C_1-C_4)$alkoxy$(C_1-C_4)$alkyl$(C_1-C)$alkylenedioxy, mono-N- or di-N,N-$(C_1-C_4)$alkylamino$(C_2-C_4)$alkoxy, 3- or 4-$(C_1-C_4)$alkoxy-(2-hydroxy)$(C_3-C_4)$alkoxy, carboxy$(C_1-C_4)$alkoxy, morpholino$(C_2-C_4)$alkoxy, imidazol-1-yl$(C_2-C_4)$alkoxy, 4$(C_1-C_4)$alkylpiperazin-1-yl-$(C_2-C_4)$alkoxy, $(C_1-C_4)$alkoxy$(C_1-C_4)$alkanoyloxy, nitro, hydroxylamino, amino, mono-N- or di-N,N-$(C_1-C_4)$alkylamino, $(C_1-C_4)$alkanoylamino, hydroxy$(C_2-C_4)$alkylamino, $(C_1-C_4)$alkoxy$(C_2-C_4)$alkylamino, $(C_1-C_4)$alkylsulfonamido, morpholino, $(C_1-C_4)$alkyl-piperazin-1-yl, bis$(C_1-C_4)$alkanesulfonamino, di-N,N-$(C_1-C_4)$alkylamino$(C_2-C_4)$alkylamino, $(C_1-C_4)$alkylamino$(C_2-C_4)$alkylamino, piperidin-1-yl, imidazol-1-yl, pyrrolidin-1-yl, $(C_1-C_4)$alkoxy$(C_1-C_4)$alkylcarbonylamino, N-$(C_1-C_4)$alkyl-N-$(C_1-C_4)$alkanoyl-amino, carboxy, $(C_1-C_4)$alkoxycarbonyl, $(C_1-C_4)$alkoxycarbonyl$(C_1-C_4)$alkoxy, amido, mono-N- or di-N,N-$(C_1-C_4)$alkylaminocarbonyl, mono-N- or di-N,N-(hydroxy$(C_2-C_4)$alkyl)aminocarbonyl, $(C_1-C_4)$alkyl, hydroxy$(C_1-C_4)$alkyl, mono-N- or di-N,N-(($C_1-C_4)$alkoxy$(C_1-C_4)$alkyl)amino$(C_1-C_4)$alkyl, mono-N- or di-N,N-$(C_1-C_4)$alkylamino$(C_1-C_4)$alkyl, $(C_1-C_4)$alkanoylamino$(C_1-C_4)$alkyl, $(C_1-C_4)$alkoxy$(C_2-C_4)$alkoxy$(C_1-C_4)$alkyl, $(C_1-C_4)$alkylthio, $(C_1-C_4)$alkoxy$(C_2-C_4)$alkylthio or hydroxy$(C_2-C_4)$alkylthio.

A third group of preferred compounds of Formula I are those compounds wherein

Z is

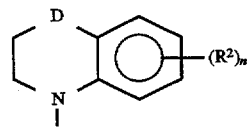

D is saturated carbon;
n is 0, 1 or 2;
$R^2$ for each occurrence is independently halo, hydroxy, amino, nitro, trifluoromethyl, ethenyl, ethynyl or $(C_1-C_4)$alkyl;
m is 0, 1 or 2; and
$R^1$ for each occurrence is substituted independently in the 6 and/or 7 positions and is hydroxy, $(C_1-C_4)$alkoxy, hydroxy$(C_2-C_4)$alkoxy, amino$(C_1-C_4)$alkyl, amino ($C_2$–$C_4$)alkoxy, ($C_1$–$C_4$)alkoxy($C_2$–$C_4$)alkoxy, ($C_1$–$C_4$)alkylenedioxy, hydroxy($C_1$–$C_4$)alkyl($C_1$–$C_4$) alkylenedioxy, ($C_1$–$C_4$)alkoxy($C_1$–$C_4$)alkyl($C_1$–$C_4$) alkylenedioxy, mono-N- or di-N-,N-($C_1$–$C_4$) alkylamino($C_2$–$C_4$)alkoxy, 3- or 4-($C_1$–$C_4$)alkoxy-(2-hydroxy)-($C_3$–$C_4$)alkoxy, carboxy($C_1$–$C_4$)alkoxy, morpholino($C_2$–$C_4$)alkoxy, imidazol-1-yl($C_2$–$C_4$) alkoxy, 4-($C_1$–$C_4$)alkylpiperazin-1-yl-($C_2$–$C_4$)alkoxy, ($C_1$–$C_4$)alkoxy($C_1$–$C_4$)alkanoyloxy, nitro, hydroxylamino, amino, mono-N- or di-N,N-($C_1$–$C_4$) alkylamino, ($C_1$–$C_4$)alkanoylamino, hydroxy($C_2$–$C_4$) alkylamino, ($C_1$–$C_4$)alkoxy($C_2$–$C_4$)alkylamino, ($C_1$–$C_4$)alkylsulfonamido, morpholino, ($C_1$–$C_4$)alkylpiperazin-1-yl, bis($C_1$–$C_4$)alkanesulfonamido, di-N,N-($C_1$–$C_4$)alkylamino($C_2$–$C_4$)alkylamino, ($C_1$–$C_4$) alkylamino($C_2$–$C_4$)alkylamino, imidazol-1-yl, piperidin-1-yl, pyrrolidin-1-yl, ($C_1$–$C_4$)alkoxy($C_1$–$C_4$) alkylcarbonylamino, N-($C_1$–$C_4$)alkyl-N-($C_1$–$C_4$) alkanoyl-amino, carboxy, ($C_1$–$C_4$)alkoxycarbonyl, ($C_1$–$C_4$)alkoxycarbonyl ($C_1$–$C_4$)alkoxy, amido, mono-N- or di-N,N-($C_1$–$C_4$)alkylaminocarbonyl, mono-N- or di-N,N-(hydroxy($C_2$–$C_4$)alkyl)aminocarbonyl, ($C_1$–$C_4$)alkyl, hydroxy($C_1$–$C_4$)alkyl, mono-N- or di-N,N-(($C_1$–$C_4$)alkoxy($C_1$–$C_4$)alkyl)amino($C_1$–$C_4$)alkyl, mono-N- or di-N,N-($C_1$–$C_4$)alkylamino($C_1$–$C_4$)alkyl, ($C_1$–$C_4$)alkanoylamino($C_1$–$C_4$)alkyl, ($C_1$–$C_4$)alkoxy ($C_2$–$C_4$)alkoxy($C_1$–$C_4$)alkyl, ($C_1$–$C_4$)alkylthio, ($C_1$–$C_4$)alkoxy($C_2$–$C_4$)alkylthio or hydroxy($C_2$–$C_4$) alkylthio.

Within this third group of preferred compounds of Formula I are those compounds wherein $R^2$ for each occurrence is independently halo, nitro, hydroxy, ($C_1$–$C_4$)alkyl or trifluoromethyl;

$R^1$ is ($C_1$–$C_4$)alkoxy, ($C_1$–$C_4$)alkylenedioxy or ($C_1$–$C_4$) alkyl;

m is 2; and n is 1 or 2.

Yet another aspect of this invention is a group of preferred compounds within the Formula I compounds, such compounds having the Formula IZ

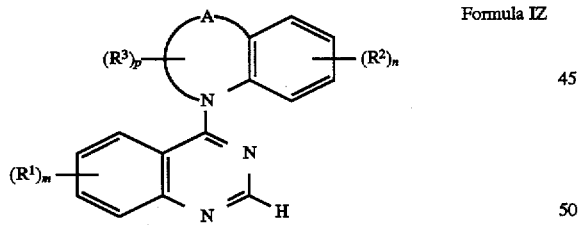

Formula IZ and the pharmaceutically acceptable salts and hydrates thereof wherein A completes a fused 5 to 9 membered mono-unsaturated, mono-aza ring, wherein said ring having 6 or more members may include an —O— or —S—;

each $R^1$ taken independently is hydrogen, trifluoromethyl, halo, nitro, hydroxy, amino, ($C_1$–$C_4$)alkyl, carboxy, ($C_1$–$C_4$)alkoxy, ($C_1$–$C_4$)alkoxy($C_1$–$C_4$)alkylene, ($C_1$–$C_4$)alkoxy($C_2$–$C_4$)alkoxy, hydroxy($C_2$–$C_4$)alkoxy, trifluoromethyloxy, ($C_1$–$C_4$)alkoxycarbonyl, ($C_1$–$C_4$) alkylenedioxy, ($C_1$–$C_4$)alkylsulfinyl, ($C_1$–$C_4$) alkylsulfonyl, pyrrolidin-1-yl, piperidin-1-yl, morpholino, 4-($C_1$–$C_4$)alkylpiperazin-1-yl, carbamoyl, N,N-di-($C_1$–$C_4$)alkylcarbamoyl, phenoxy, benzyloxy, hydroxyamino, ($C_1$–$C_4$)alkoxyamino, N,N-di-($C_1$–$C_4$) alkylamino, ($C_1$–$C_4$) alkoxycarbonylamino, ($C_1$–$C_4$) alkanoylamino, carbamoylamino or benzoylamino, said phenoxy, benzyloxy and benzoylamino optionally mono-substituted with halo, nitro, trifluoromethyl, hydroxy or ($C_1$–$C_4$)alkyl and said ($C_1$–$C_4$) alkylenedioxy is linked at both ends to the quinazoline moiety;

each $R^2$ taken independently is hydrogen, trifluoromethyl, halo, nitro, hydroxy, amino, ($C_1$–$C_4$)alkyl, ($C_1$–$C_4$) alkoxy, benzyloxy, phenoxy, ($C_1$–$C_4$)alkylenedioxy, cyano, benzoylamino, ($C_1$–$C_4$)alkanoyl, N,N-di-($C_1$–$C_4$)alkylamino, ($C_1$–$C_4$)alkylthio, ($C_1$–$C_4$) alkylsulfinyl or ($C_1$–$C_4$)alkylsulfonyl, said benzyloxy, phenoxy and benzoylamino optionally mono-substituted with halo, nitro, trifluoromethyl, hydroxy or ($C_1$–$C_4$)alkyl and said ($C_1$–$C_4$)alkylenedioxy is linked at both ends to the benzene moiety;

each $R^3$ taken independently is hydroxy, N,N-di-($C_1$–$C_4$) alkylamino, sulfo, ($C_1$–$C_4$)alkoxy, provided that such groups are not attached to a ring carbon which is adjacent to an —O— or —S— and that such groups are not at the 2 position, carboxy, hydroxy($C_1$–$C_3$) alkylene, ($C_1$–$C_4$)alkoxy($C_1$–$C_3$)alkylene, N,N-di-($C_1$–$C_4$)alkylamino($C_1$–$C_3$)alkylene, carboxy($C_1$–$C_3$) alkylene, ($C_1$–$C_4$)alkoxycarbonyl or sulfo($C_1$–$C_3$) alkylene;

n is 1 or 2;

p is 0, 1 or 2; and m is 1, 2 or 3.

Other compounds within the scope of this invention include:

(6-Chloro-1-(6,7-methylenedioxy-quinazolin-4-yl)-2,3-dihydro-1H-indol-5-yl)-methylamine, 3-(6-Chloro-1-(6,7-bis-(2-hydroxy-ethoxy)-quinazolin-4-yl)-2,3-dihydro-1H-indol-3-yl)-propanol, 3-(4-(6-Fluoro-7-methyl-2,3-dihydro-indol-1-yl)-7-(3-hydroxy-propoxy)-quinazolin-6-yloxy)-propan-1-ol, 6-Amino-7-hydroxymethyl-4-(6-vinyl-2,3-dihydro-indol-1-yl)-quinazoline, 4-(6-Ethyl-2,3-dihydro-indol-1-yl)-7-methoxy-6-methyl-quinazoline, 1-(6,7-Dimethoxy-quinazolin-4-yl)-6-chloro-2,3-dihydro-1H-indol-4-ol, (4-(6-Bromo-3-(3-morpholin-4-yl-propyl)-2,3-dihydro-indol-1-yl)-quinazolin-6-yl)-methyl-amine, (4-(6-Chloro-3-(3-dimethylamino-propyl)-2,3-dihydro-indol-1-yl)-7-methoxy-quinazolin-6-yl)-methanol, 3-(1-(6,7-Bis-(2-methoxy-ethoxy)-quinazolin-4-yl)-6-fluoro-7-methyl-2,3-dihydro-1H-indol-3-yl)-propionic acid, 2-(4-(3-(3-Dimethylamino-propyl)-3,5,6,7-tetrahydro-2H-pyrrolo[2,3-f]indol-1-yl)-7-(2-hydroxy-ethoxy)-quinazolin-6-yloxy)-ethanol, (2-(6-Chloro-1-(2,2-dimethyl-(1,3)dioxolo[4,5-g] quinazolin-8-yl)-2,3-dihydro-1H-indol-3-yl)-ethyl)-diethyl-amine, N-(4-(6-Ethynyl-7-methyl-2,3-dihydro-indol-1-yl)-7-methoxy-quinazolin-6-ylmethyl)-acetamide, 3-(4-(6-Bromo-7-methyl-2,3-dihydro-indol-1-yl)-6-trifluoromethoxy-quinazolin-7-yloxy)-propan-1-ol, 3-(6-Chloro-1-(6,7-bis-(2-methoxy-ethoxy)-quinazolin-4-yl)-2,3-dihydro-1H-indol-3-yl)-methanol, 6-Chloro-1-(7-(2-dimethylamino-ethoxy)-quinazolin-4-yl)-2,3-dihydro-1H-indol-4-ol and 3-(4-(6-Chloro-4-methylamino-2,3-dihydro-indol-1-yl)-6-(3-hydroxy-propoxy)-quinazolin-7-yloxy)-propan-1-ol.

Yet another aspect of this invention is directed to a method for treating a hyperproliferative disorder in a mammal by administering to a mammal suffering from a hyperproliferative disorder, a hyperproliferative disorder treating amount of a Formula I compound.

This invention is also directed to pharmaceutical compositions for the treatment of a hyperproliferative disorder in mammals which comprise a hyperproliferative disorder treating amount of a compound of the Formula I and a pharmaceutically acceptable carrier.

By halo is meant chloro, bromo, iodo, or fluoro.

By alkyl is meant straight chain or branched saturated hydrocarbon.

By mono-unsaturated is meant that the A ring's only unsaturated bond is the bond shared with the benzene ring.

Those carbons whose substituents are not otherwise specified are attached to hydrogen (i.e., so that carbon is neutral and possesses a completed octet).

As used herein, the expression "reaction-inert solvent" refers to a solvent which does not interact with starting materials, reagents, intermediates or products in a manner which adversely affects the yield of the desired product.

One of ordinary skill will recognize that certain substituents listed in this invention will be chemically incompatible with one another or with heteroatoms in the compounds, and will avoid these incompatibilities in selecting compounds of this invention.

Other features and advantages will be apparent from the specification and claims which describe the invention.

DETAILED DESCRIPTION OF THE INVENTION

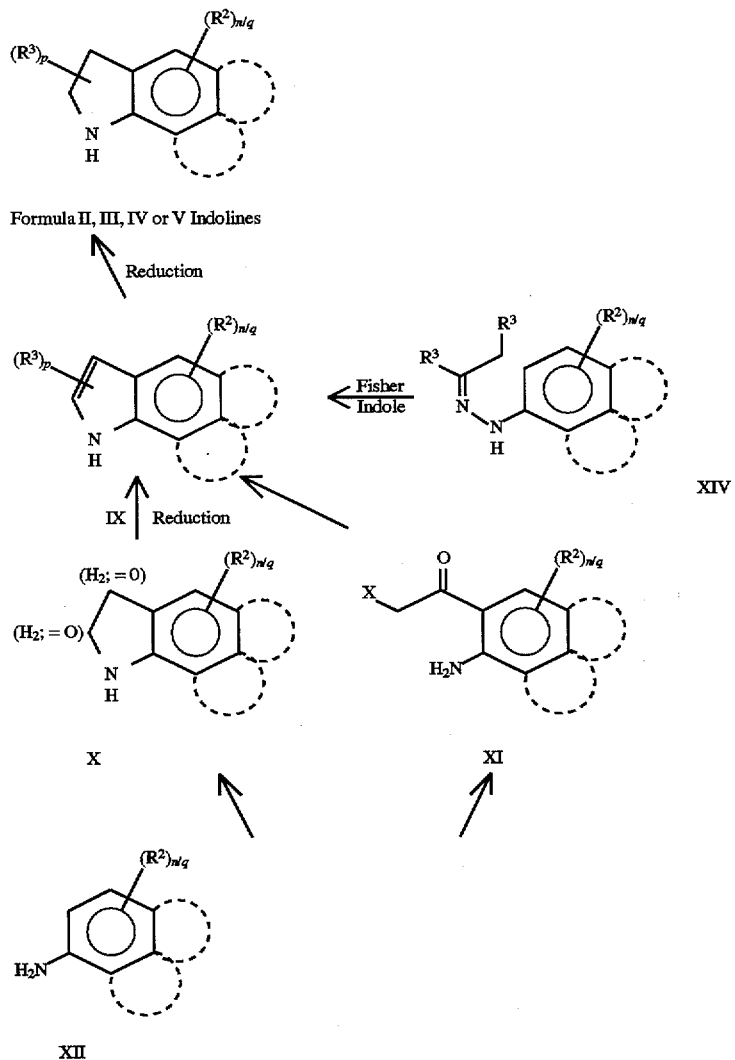

The Formula I compounds, or a pharmaceutically acceptable salt thereof may be prepared by any process known to be applicable to the preparation of chemically-related compounds.

In general the Formula I quinazolines may be made by preparing the 4-amino adjunct of the appropriately substituted quinazoline using the appropriately substituted mine.

Typically the appropriately substituted 4-haloquinazoline (or a quinazoline bearing a suitable displaceable leaving group in the 4-position such as aryloxy, alkyl sulfonyloxy such as trifluoromethanesulfonyloxy, arylsulfonyloxy, trialkyl-siloxy, cyano, pyrazolo, triazolo or tetrazolo), preferably a 4-chloroquinazoline, is combined with the appropriate amine in a solvent such as a $(C_1-C_a)$alcohol, dimethylformamide, N-methylpyrrolidin-2-one, chloroform, acetonitrile, tetrahydrofuran (THF), 1,4-dioxane, dimethylsulfoxide or other aprotic solvent. This combination may occur in the presence of a base, and it is preferred that this combination occurs in the presence of an alkali or alkaline earth metal carbonate or hydroxide, or a tertiary amine base, such as pyridine, 2,6-lutidine, collidine, N-methyl-morpholine, triethylamine, diisopropylethylamine, 4-dimethylamino-pyridine or N,N-dimethylaniline. These bases are hereinafter referred to as suitable bases. The mixture is maintained at a temperature of about ambient to about reflux, preferably about 35° C. to about reflux, until substantially no remaining 4-haloquinazoline can be detected, typically about 2 hours to about 24 hours. Preferably, the reaction is performed under an inert atmosphere such as dry nitrogen gas.

Generally the reactants are combined stoichiometrically when an amine base is used (alternatively, if an amine base is not used an excess of the amine may be used) however, for those compounds where a salt (typically HCl) of an amine is used, it is preferable to use excess amine base, generally an extra equivalent of amine base.

For those compounds where a sterically hindered amine (such as a 2-alkyl-indoline) or very reactive 4-haloquinazoline is used it is preferable to use t-butyl alcohol or a polar aprotic solvent such as dimethylformamide, dimethylacetamide, or N-methylpyrolidin-2-one as the solvent.

The following paragraphs facilitate the synthesis of many of the Formula I compounds by appropriate reactions subsequent to the above coupling.

For the production of those compounds of Formula I wherein $R^1$ is an amino or hydroxyamino the reduction of a Formula I compound wherein $R^1$ is nitro is employed.

The reduction may conveniently be carried out by any of the many procedures known for such transformations. The reduction may be carried out, for example, by the hydrogenation of a solution of the nitro compound in a reaction-inert solvent in the presence of a suitable metal catalyst such as palladium or platinum. Further suitable reducing agents are, for example, sodium dithionite in formic acid or an activated metal such as activated iron (produced by washing iron powder with a dilute solution of an acid such as hydrochloric acid). Thus, for example, the reduction may be carried out by heating a mixture of the nitro compound and the activated metal in a solvent such as a mixture of water and an alcohol, for example, methanol or ethanol, to a temperature in the range, for example, 50° to 150° C., conveniently at or near 70° C..

For the production of those compounds of Formula I wherein $R^2$ is an amino, the reduction of a Formula I compound wherein $R^2$ is nitro may be used.

For the production of those compounds of Formula I wherein $R^2$ or $R^3$ incorporates a primary or secondary amino moiety (other than that amine intended to react with the quinazoline), such free amine is preferably protected prior to the above described reaction followed by deprotection, subsequent to the above described reaction with 4-haloquinazoline.

For a description of protecting groups and their use, see T. W. Greene and P. G. M. Wuts, "Protective Groups in Organic Synthesis", Second Ed., John Wiley & Sons, New York, 1991.

Several well known nitrogen protecting groups can be used. Such groups include $(C_1-C_6)$alkoxycarbonyl, optionally substituted benzyloxycarbonyl, aryloxycarbonyl, trityl, vinyloxycarbonyl, o-nitrophenylsulfonyl, diphenylphosphinyl, p-toluenesulfonyl, and benzyl, The addition of the nitrogen protecting group may be carried out in a chlorinated hydrocarbon solvent such as methylene chloride or 1,2dichloroethane, or an ethereal solvent such as glyme, diglyme or THF, in the presence or absence of a tertiary amine base such as triethylamine, diisopropylethylamine or pyridine, preferably triethylamine, at a temperature from about 0° C. to about 50° C., preferably about ambient temperature. Alternatively, the protecting groups are conveniently attached using Schotten-Baumann conditions.

Subsequent to the above described amine coupling reaction the protecting group may be removed by deprotecting methods known to those skilled in the art such as trifluoroacetic acid in methylene chloride for the tert-butoxycarbonyl protected products.

For the production of those compounds of the Formula I wherein $R^1$ is hydroxy, the cleavage of a Formula I compound wherein $R^1$ is $(C_1-C_4)$alkoxy is preferred.

The cleavage reaction may conveniently be carried out by any of the many procedures known for such a transformation. Treatment of the quinazoline derivative of Formula I with molten pyridine hydrochloride (20–30 eq.) at 150° to 175° C. may be employed for such O-dealkylations. Alternatively, the reaction may be carried out, for example, by treatment of the quinazoline derivative with an alkali metal $(C_1-C_4)$alkylsulphide such as sodium ethanethiolate or, for example, by treatment with an alkali metal diarylphosphide such as lithium diphenylphosphide. Alternatively the cleavage reaction may conveniently be carded out, for example, by treatment of the quinazoline derivative with a boron or aluminum trihalide such as boron tribromide. Such reactions are preferably carried out in the presence of a reaction-inert solvent and at a suitable temperature.

For the production of those compounds of Formula I wherein $R^1$ or $R^2$ is a $(C_1-C_4)$alkylsulphinyl or $(C_1-C_4)$alkylsulphonyl group, the oxidation of a Formula I compound wherein $R^1$ or $R^2$ is a $(C_1-C_4)$alkylthio group is preferred.

A suitable oxidizing agent is, for example, an agent known in the art for the oxidation of thio to sulphinyl and/or sulphonyl, for example, hydrogen peroxide, a peracid (such as 3-chloroperbenzoic, performic or peracetic acid), an alkali metal peroxysulphate (such as potassium peroxymonosulphate), chromium trioxide or gaseous oxygen in the presence of platinum. The oxidation is generally carried out under as mild conditions as possible and with the required stoichiometric amount of oxidizing agent in order to reduce the risk of over oxidation and damage to other functional groups. In general the reaction is carried out in a suitable solvent such as methylene chloride, chloroform, acetone, tetrahydrofuran or tert-butyl methyl ether and at a temperature, for example, −25° to 50° C., conveniently at or near ambient temperature, that is in the range of 15° to 35° C. When a compound carrying a sulphinyl group is required a milder oxidizing agent may also be used, for example sodium or potassium metaperiodate, conveniently in a polar solvent such as acetic acid or ethanol. It will be appreciated that when a compound of the Formula I containing a $(C_1-C_4)$alkylsulphonyl group is required, it may be obtained by oxidation of the corresponding $(C_1-C_4)$alkylsulphinyl compound as well as of the corresponding $(C_1-C_4)$alkylthio compound.

For the production of those compounds of Formula I wherein $R^1$ is $(C_2-C_4)$alkanoylamino or substituted $(C_2-C_4)$ alkanoylamino, ureido, 3-phenylureido, benzamido, or sulfonamido, the acylation or sulfonation of a Formula I compound wherein $R^1$ is amino is appropriate.

A suitable acylating agent is, for example, any agent known in the art for the acylation of amino to acylamino, for example an acyl halide (e.g., a $(C_2-C_4)$alkanoyl chloride or bromide or a benzoyl chloride or bromide), an alkanoic acid anhydride or mixed anhydride (e.g., $(C_2-C_4)$alkanoic acid anhydride such as acetic anhydride or the mixed anhydride formed by the reaction of an alkanoic acid and a $(C_1-C_4)$ alkoxycarbonyl halide, for example $(C_1-C_4)$alkoxycarbonyl chloride, in the presence of a suitable base). For the production of those compounds of Formula I wherein $R^1$ is ureido or 3-phenylureido, a suitable acylating agent is, for example, a cyanate, for example an alkali metal cyanate such as sodium cyanate or, for example, an isocyanate such as phenyl isocyanate. N-Sulfonylations may be carried out with suitable sulfonyl halides or sulfonylanhydrides in the presence of a tertiary amine base. In general the acylation or sulfonylation is carried out in a reaction-inert solvent and at a temperature, in the range, for example, −30° to 120° C., conveniently at or near ambient temperature.

For the production of those compounds of Formula 1 wherein $R^1$ is $(C_1-C_4)$alkoxy or substituted $(C_1-C_4)$alkoxy or $R^1$ is $(C_1-C_4)$alkylamino or substituted mono-N- or di-N,N-$(C_1-C_4)$alkylamino, the alkylation, preferably in the presence of a suitable base, of a Formula I compound wherein $R^1$ is hydroxy or amino as appropriate may be preferred.

A suitable alkylating agent is, for example, any agent known in the art for the alkylation of hydroxy to alkoxy or substituted alkoxy, or for the alkylation of amino to alkylamino or substituted alkylamino, for example an alkyl or substituted alkyl halide, for example a $(C_1-C_4)$alkyl chloride, bromide or iodide or a substituted $(C_1-C_4)$alkyl chloride, bromide or iodide, in the presence of a suitable base in a reaction-inert solvent and at a temperature in the range, for example, 10° to 140° C., conveniently at or near ambient temperature.

For the production of those compounds of Formula I wherein $R^1$ is an amino-, oxy- or cyano-substituted $(C_1-C_4)$ alkyl substituent, the reaction, preferably in the presence of a suitable base, of a Formula I compound wherein $R^1$ is a $(C_1-C_4)$alkyl substituent bearing a displaceable group with an appropriate amine, alcohol or cyanide is appropriate. The reaction is preferably carried out in a reaction-inert solvent or diluent and at a temperature in the range, for example, 10° to 100° C., conveniently at or near ambient temperature.

For the production of those compounds of Formula I wherein $R^1$, $R^2$, or $R^3$ is a carboxy substituent or a substituent which includes a carboxy group, the hydrolysis of a Formula I compound wherein the respective $R^1$, $R^2$ or $R^3$ is a $(C_1-C_4)$alkoxycarbonyl substituent or a substituent which includes a $(C_1-C_4)$alkoxycarbonyl group is desirable.

The hydrolysis may conveniently be performed, for example, under basic conditions such as an alkali metal hydroxide mediated hydrolysis as illustrated in the accompanying Examples.

For the production of those compounds of Formula I wherein $R^1$ is amino, $(C_1-C_4)$alkylamino, di-[$(C_1-C_4)$alkyl] amino, pyrrolidin-1-yl, piperidino, morpholino, piperazin-1-yl, 4-$(C_1-C_4)$alkylpiperazin-1-yl or $(C_1-C_4)$alkythio, the reaction, conveniently in the presence of a suitable base, of a Formula I compound wherein $R^1$ is a displaceable group with an appropriate amine or thiol may be preferred.

The reaction is preferably carried out, usually in the presence of a suitable base, in a reaction-inert solvent or diluent and at a temperature in the range, for example, 10° to 180° C., conveniently in the range 100° to 150° C.

For the production of those compounds of Formula I wherein $R^1$ is 2-oxopyrrolidin-1-yl or 2-oxopiperidin-1-yl, the cyclisation, in the presence of a suitable base, of a Formula I compound wherein $R^1$ is a halogen-$(C_2-C_4)$ alkanoylamino group is convenient.

The reaction is preferably carded out, usually in the presence of a suitable base, in a reaction-inert solvent or diluent and at a temperature in the range, for example, 10° to 100° C., conveniently at or near ambient temperature.

For the production of compounds of Formula I in which $R^1$ is carbamoyl, substituted carbamoyl, alkanoyloxy or substituted alkanoyloxy, the carbamoylation or acylation of a Formula I compound wherein $R^1$ is hydroxy is convenient.

Suitable acylating agents are for example any agent known in the art for acylation of hydroxyaryl moieties to alkanoyloxy aryl. For example, $(C_2-C_4)$alkanoyl halides, $(C_2-C_4)$alkanoyl anhydrides or mixed anhydrides, and suitable substituted derivatives thereof may be employed, typically in the presence of a suitable base. Alternatively, $(C_2-C_4)$alkanoic acids or suitably substituted derivatives thereof may be coupled with a Formula I compound wherein $R^1$ is hydroxy with the aid of a condensing agent such as a carbodiimide. For the production of those compounds of Formula I in which $R^1$ is carbamoyl or substituted carbamoyl, suitable carbamoylating agents are for example a cyanate or an alkyl or aryl isocyanate, typically in the presence of a suitable base. Alternatively a suitable intermediate such as the chloroformate, succinimido carbonate, or imidazolocarbonyl derivative of a quinazoline of Formula I in which $R^1$ is hydroxy may be generated, for example by treatment of said derivative with phosgene (or a phosgene equivalent), disuccinimidocarbonate, or carbonyldiimidazole. The resulting intermediate may then be reacted with an appropriate amine or substituted amine to produce the desired carbamoyl derivatives.

For the production of quinazoline derivatives of Formula I wherein $R^1$ is aminocarbonyl or a substituted aminocarbonyl, the aminolysis of a suitable intermediate derived from a quinazoline of Formula I in which $R^1$ is carboxy is preferred.

The activation and coupling of a Formula I compound wherein $R^1$ is carboxy may be performed by a variety of methods known to those skilled in the art. Suitable methods include activation of the carboxyl as an acid halide, azide, symmetric or mixed anhydride, or active ester of appropriate reactivity for coupling with the desired amine. Examples of such types of intermediates and their production and use in couplings with mines may be found extensively in the literature; for example M. Bodansky and A. Bodansky, "The Practice of Peptide Synthesis", Springer,-Verlag, New York, 1984.

The resulting Formula I compounds may be isolated and purified by standard methods, such as solvent removal and recrystallization or chromatography, if desired.

The starting materials for the above described reaction schemes (e.g., mines, quinazolines, amine protecting groups) are readily available or can be easily synthesized by those skilled in the art using conventional methods of organic synthesis. For example, the preparation of 2,3-dihydro-1,4-benzoxazine derivatives are described in R. C. Elderfield, W. H. Todd, S. Gerber, Ch. 12 in "Heterocyclic Compounds", Vol. 6, R. C. Elderfield ed., John Wiley and Sons, Inc., N.Y., 1957. Substituted 2,3-dihydrobenzothiazinyl compounds are described in R. C. Elderfield and E. E. Harris, Ch. 13 in Volume 6 of the Elderfield "Heterocyclic Compounds" book. The synthesis of 1,2,3,4-tetrahydroquinolines and their quinoline precursors are described in for example, "The Chemistry of Heterocyclic Compounds", Vol. 32, Parts 1,2 and 3, G. Jones, ed., John Wiley and Sons, N.Y., 1977. Alkyl and aryl-substituted 1,2,3,4-tetrahydroquinolines were typically prepared by the catalytic hydrogenation of the appropriately substituted quinolines using $Pt_2O/H_{2(g)}$ in MeOH (for example by the procedure of M. Honel and F. W. Vierhapper, J. Chem. Soc., Perkin I 1980, 1933–1939). The synthesis of substituted 2,3,4,5-tetrahydro-1H-benzo(b)azepines is described in G. R. Proctor, Ch. II, Vol.43, "The Chemistry of Heterocyclic Compounds", Part I, A. Rosowsky, ed., Wiley Interscience, N.Y. 1984. Certain substituted 2,3,4,5-tetrahydro-1H-1-benzo[b]azepin-2-ones and 1,2,3,4,5,6-hexahydro-1-benzo[b]azocin-2-ones which are readily reduced to the corresponding 2,3,4,5-tetrahydro-1H-benzo[b]azepines and 1,2,3,4,5,6-hexahydro-1-benzo-[b]azocines, respectively are described in E. C. Homing et al, J. Am. Chem. Soc. 74, 5153 (1952), and R. Huisgen et al, Liebigs Ann. Chem. 586, 30 (1954).

In addition, the following general description in conjunction with Reaction Scheme I and the Preparations (which can be analogized therefrom) are provided as an additional aid to the preparation of the indoline based mines.

Thus, according to Scheme I the desired Formula II, III, IV or V indoline based compounds may be conveniently prepared by reduction of the corresponding Formula IX indole based compounds (the dotted line circles refer to the fused monocyclic and bicyclic moieties of Formulas III, IV and V).

In general, the Formula IX compounds bearing aprotic $R^2$ or $R^3$ substituents are treated with $ZnBH_4$ (prepared from $ZnCl_2$ and $NaBH_4$ according to W. J. Gensler et al., J. Am. Soc. 82, 6074–6081 (1960)) in an etheral solvent such as diethyl ether at a temperature of about 10° C. to about 40° C., preferably at ambient. Such treatment is described in H. Korsuki et al., Heterocycles 26, 1771–1774 (1987). Alternatively, the Formula IX compounds may be treated with a borane/pyridine complex (or other borane/tertiary amine complex) in the absence of solvent, or presence of solvent, such as tetrahydrofuran at a temperature of about 10° C. to about 30° C., preferably at ambient, followed by treatment of the mixture with an acid such as hydrochloric acid, trifluoroacetic acid or acetic acid to provide compounds of Formula II, III, IV or V.

The desired Formula IX compounds wherein p is one or two may be prepared from the appropriate Formula XIV compound via a Fisher Indole synthesis or modification thereof ("The Fischer Indole Synthesis", B. Robinson, Wiley Interscience, N.Y., 1982; or alternatively U. Pindur, R. Adam, J. Het. Chem. 25, 1–8 (1988) and references therein).

The Formula IX indoles wherein p is zero may typically be prepared from the Formula XII aniline-type compounds from either of two mutes: via the Formula X compounds or the Formula XI compounds. However, the route via Formula XI compound is not preferred for preparation of nitro or carboalkoxy substituted indoles.

Thus, the desired Formula IX compound may be prepared from the appropriate Formula X compound (e.g., isatins, oxindoles) by reduction, or from the appropriate Formula XI compound via a reductive cyclization. In general the Formula X compound is treated with borane in an etheral solvent such as tetrahydrofuran at a temperature of about 0° C. to about 30° C., preferably ambient. Generally the Formula XI compound is treated with sodium borohydride in an etheral solvent such as dioxane at a temperature of about 20° C. to about 100° C., preferably reflux.

The desired Formula X isatin compound may be prepared from the appropriate Formula XII compound by combination with chloral hydrate and hydroxylamine followed by an acid catalyzed cyclization, such process being adapted from Org. Syn., Coll. Vol. I, 327–330.

The desired Formula XI compound may be prepared from the appropriate Formula XII compound by a Lewis acid catalyzed ortho-acylation. The typical preparation is adapted from T. Sugasawa et al., J. Org. Chem. 44 (4), 578–586 (1979). In general, the Formula XII compound is reacted with 2-chloroacetonitrile in the presence of boron trichloride and an auxiliary acid catalyst such as aluminum chloride, typically in an aromatic solvent such as xylene, toluene or chlorobenzene at a temperature of about 50° C. to about reflux.

The desired Formula XII aminoaromatic compounds may be prepared from the appropriate corresponding nitroaromatic compounds by various reductive methods (such as those given above).

Alternatively, some of the desired Formula II, III, IV or V indoline-based compounds may be prepared from other of the above described indoline-based compounds by further modification prior to combination with the quinazoline moieties of Formula I.

For example, the appropriately substituted desired 5-hydroxyindole may be prepared from the corresponding indolines by hydroxylation according to an adaptation of the procedure of H. J. Teuber and G. Staiger, Chem. Ber. 89,489–508 (1955) followed by reduction to achieve the corresponding 5-hydroxyindoline. Generally, potassium nitrosodisulfonate in aqueous phosphate buffer is added to the appropriately substituted indoline in acetone at neutral pH at a temperature of about 0° C. to about 25° C. to produce the 5-hydroxyindole derivative, which may be subsequently reduced with borane/pyridine/aqueous HCl to afford the 5-hydroxyindoline.

The appropriately substituted desired bromoindolines (e.g., in the 4- or 6position) may be prepared from the corresponding indolines by bromination analogous to the procedure described by: Y. Miyake and Y. Kikugawa, J. Het. Chem. 20, 349–352 (1983). This procedure may also be utilized for brominations of other larger rings (e.g., 1,2,3,4-tetrahydroquinolines, 2,3,4,5-tetrahydro-1H-benzo[b]azepines and 1,2,3,4,5,6-hexahydro-benzo[b]azocines, particularly in the 5/7, 6/8, and 7/9-positions). Generally, the appropriately substituted indoline is reacted with bromine in the presence of a halophile such as silver sulfate under strongly acidic conditions at 0° C. to 25° C.

In addition, certain indolines with or without 3-alkyl substituents may conveniently be prepared from the appropriate 2-(2-halophenyl)alkylamines according to the German patent application DE 3424900A1.

In addition, hydroxyalkylindolines can be prepared by reduction of the appropriate carboxylic acids or their esters, for example according to E. J. Corey et. al, J. Am. Chem. Soc. 92 (8), 2476–2488 (1970).

The appropriately substituted desired alkyl, alkenyl or allylic substituted indolines may be prepared from the corresponding trialkylsilyl-protected 4-, 5- or 6-haloindolines via a Nickel-phosphine catalyzed Grignard addition analogous to the general procedure described by K. Tamao et al., Bull. Chem. Soc. Japan 49, 1958–1969 (1976). Generally, the indoline is N-protected by reaction with tert-butyldimethylsilyltriflate in a halogenated solvent in the presence of a tertiary amine. The N-silylated halo-indoline is subsequently reacted with the appropriate alkyl, alkenyl or allylic Grignard in an etheral solvent in the presence of a suitable nickel-phosphine complex, typically [Ni(dppe)Cl$_2$]. Subsequent treatment with methanol containing a trace of acid such as trifuoroacetic acid, or with fluoride anion in a suitable solvent such as THF, liberates the desired indoline product.

In addition, the desired substituted alkenyl- or alkynyl-indolines may be prepared by the palladium-catalyzed vinylation or alkynylation of the appropriate 4-, ,5-, 6- or 7-haloindoline, for example, according to references reviewed by V. N. Kalinin, Synthesis 1991, 413–432. For example, for alkynylindolines, generally the corresponding bromo- or iodoindoline in diethylamine is treated with an alkyl-, appropriately substituted alkyl, or trimethylsilylacetylene in the presence of catalytic mounts of CuI and Pd(PPh$_3$)$_4$ at reflux.

Further, in addition to the nonlimiting examples provided herein the preparation of various indolines, indoles, oxindoles, and isatins useful as intermediates are further described in "Heterocyclic Compounds with Indole and Carbazole Systems", W. C. Sumpter and F. M. Miller, in Vol. 8 of "The Chemistry of Heterocyclic Compounds" Series, Interscience Publishers Inc., N.Y., 1954 and references contained therein.

Certain Formula I quinazolines can exist in solvated as well as unsolvated forms such as, for example, hydrated forms. It is to be understood that the invention encompasses all such solvated as well as unsolvated forms which possess activity against hyperproliferative diseases.

A suitable pharmaceutically-acceptable salt of a quinazoline derivative of the invention is, for example, an acid-addition salt of a quinazoline derivative of the invention which is sufficiently basic, for example an acid-addition salt with, for example, an inorganic or organic acid, for example, hydrochloric, hydrobromic, sulphuric, phosphoric, methanesulfonic, benzenesulfonic, trifluoroacetic, citric, lactic or maleic acid. In addition a suitable pharmaceutically-acceptable base-addition salt of a quinazoline derivative of the invention which is sufficiently acidic is an alkali metal salt, for example a lithium, sodium or potassium salt; an alkaline earth metal salt, for example a calcium or magnesium salt; an ammonium salt; or a salt with an organic base which affords a physiologically-acceptable cation for example a salt with methylamine, dimethylamine, trimethylamine, piperidine, morpholine or tris-(2-hydroxyethyl)amine. All such salts are within the scope of this invention and they can be prepared by conventional methods. For example, they can be prepared simply by contacting the acidic and basic entities, usually in a stoichiometric ratio, in either an aqueous, non-aqueous or partially aqueous medium, as appropriate. The salts are recovered either by filtration, by precipitation with a non-solvent, preferably an etheral or hydrocarbon solvent, followed by filtration, by evaporation of the solvent, or, in the case of aqueous solutions, by lyophilization, as appropriate.

Some of the compounds of Formula I incorporate asymmetric carbon atoms. Diastereomeric mixtures can be separated into their individual diastereomers on the basis of their physical chemical differences by methods known per se., for example, by chromatography and/or fractional crystallization. Enantiomers can be separated by converting the enantiomeric mixtures into a diastereomeric mixture by reaction with an appropriate optically active compound (e.g., alcohol or acid), separating the diastereomers and converting (e.g., hydrolyzing) the individual diastereomers to the corresponding pure enantiomer. Alternatively, enantiomers may be resolved by differential crystallizations as diastereomeric salts. All such isomers, including diastereomers and enantiomers are considered as pert of the invention.

The compounds of this invention are potent inhibitors of the erbB family of oncogenic and protooncogenic protein tyrosine kinases such as epidermal growth factor receptor (EGFR), erbB2, HER3, or HER4 and thus are all adapted to therapeutic use as antiproliferative agents (e.g., anticancer) in mammals, particularly humans. In particular, the compounds of this invention are therapeutants or prophylactics for the treatment of a variety of benign or malignant human tumors (renal, liver, kidney, bladder, breast, gastric, ovarian, colorectal, prostate, pancreatic, lung, vulval, thyroid, hepatic carcinomas, sarcomas, glioblastomas, various head and neck tumors), and other noncancerous hyperplastic disorders such as benign hyperplasia of the skin (e.g., psoriasis) or prostate (e.g., BPH). Such activity against benign disorders can be determined by standard assays such as described in J. Invest. Dermatol. 98, 296–301 (1992). It is in addition expected that a quinazoline of the present invention may possess activity against a range of leukemias and lymphoid malignancies.

The compounds of Formula I also potentiate responses to conventional cancer chemotherapies and radiotherapy in a dose and schedule-dependent manner based upon the substantial synergy observed between neutralizing anti-EGFR antibodies and conventional chemotherapeutants (J. Baselga et al., J. Nat. Cancer Inst. 85, 1327–1333 (1993); Z. Fan et al., Cancer. Res. 53, 4637–4642 (1993)).

The compounds of Formula I may also be expected to be useful in the treatment of additional disorders in which aberrant expression, ligand/receptor interactions, activation, or signalling events related to various protein tyrosine kinases, whose activity is inhibited by the agents of Formula I, are involved.

Such disorders may include those of neuronal, glial, astrocytal, hypothalamic, and other glandular, macrophagal, epithelial, stromal, and blastocoelic nature in which aberrant function, expression, activation or signalling of the erbB tyrosine kinases may be involved. In addition, compounds of Formula I may have therapeutic utility in inflammatory, angiogenic and immunologic disorders involving both identified and as yet unidentified tyrosine kinases which are inhibited by compounds of Formula I.

The in vitro activity of these compounds in inhibiting the receptor tyrosine kinase (and thus subsequent proliferative response, e.g., cancer) may be determined by a procedure as detailed below.

Activity of compounds of Formula I in vitro can be determined by the amount of inhibition of the phosphorylation of an exogenous substrate (e.g., Lys$_3$-Gastrin or polyGluTyr (4:1) random copolymer (I. Posner et. al., J. Biol. Chem. 267 (29), 20638–47 (1992)) on tyrosine by epidermal growth factor receptor kinase by a test compound relative to a control. Affinity purified, soluble human EGF receptor (96 ng) is obtained according to the procedure in G. N. Gill, W. Weber, Methods in Enzymology 146, 82–88 (1987) from A431 cells (American Type Culture Collection, Rockville, Md.) and preincubated in a microfuge tube with EGF (2 μg/ml) in phosphorylation buffer+vanadate (PBV: 50 mM HEPES, pH 7.4; 125 mM NaCl; 24 mM $MgCl_2$; 100 μM sodium orthovanadate), in a total volume of 10 μl, for 20–30 minutes at room temperature. The test compound, dissolved in DMSO, is diluted in PBV, and 10 μl is mixed with the EGF receptor/EGF mix, and incubated for 10–30 minutes at 30° C. The phosphorylation reaction is initiated by addition of 20 μl $^{33}$P-ATP/substrate mix (120 μM $Lys_3$-Gastrin (sequence in single letter code for amino acids, KKKGPWLEEEEEAYGWLDF), 50 mM Hepes pH 7.4, 40 μM ATP, 2 μCi y-[$^{33}$P]-ATP) to the EGFr/EGF mix and incubated for 20 minutes at room temperature. The reaction is stopped by addition of 10 μl stop solution (0.5M EDTA, pH 8; 2 mM ATP) and 6 μl 2N HCl. The tubes are centrifuged at 14,000 RPM, 4° C., for 10 minutes. 35 μl of supernatant from each tube is pipetted onto a 2.5 cm circle of Whatman P81 paper, bulk washed four times in 5% acetic acid, 1 liter per wash, and then air dried. This results in the binding of substrate to the paper with loss of free ATP on washing. The [$^{33}$P] incorporated is measured by liquid scintillation counting. Incorporation in the absence of substrate (e.g., $lys_3$-gastrin) is subtracted from all values as a background and percent inhibition is calculated relative to controls without test compound present.

Activity of compounds of Formula I in vivo can be determined by the amount of inhibition of tumor growth by a test compound relative to a control. The tumor growth inhibitory effects of various compounds are measured according to the methods of Corbett, T. H., et al. "Tumor Induction Relationships in Development of Transplantable Cancers of the Colon in Mice for Chemotherapy Assays, with a Note on Carcinogen Structure", *Cancer Res.*, 35, 2434–2439 (1975) and Corbett, T. H., et al., "A Mouse Colon-tumor Model for Experimental Therapy", *Cancer Chemother. Rep. (Part 2)*", 5, 169–186 (1975), with slight modifications. Tumors are induced in the left flank by s.c. injection of 1×10$^6$ log phase cultured tumor cells (human MDA-MB-468 breast or human HN5 head and neck carcinoma cells) suspended in 0.10 ml RPMI 1640. After sufficient time has elapsed for the tumors to become palpable (2–3 mm in diameter) the test animals (athymic mice) are treated with compound (formulated by dissolution in DMSO typically at a concentration of 50 to 100 mg/mL followed by 1:9 dilution into 0.1% Pluronic® P105 in 0.9% saline) by the intraperitoneal (ip) or oral (po) routes of administration twice daily (i.e., every 12 hours) for 5 consecutive days. In order to determine a tumor growth inhibition, the tumor is measured in millimeters with Vernier calipers across two diameters and the tumor size (mg) is calculated using the formula: Tumor weight (TuW)=(length×[width]$^2$)/2, according to the methods of Geran, R. I., et al. "Protocols for Screening Chemical Agents and Natural Products Against Animal Tumors and Other Biological Systems", Third Edition, *Cancer Chemother. Rep.*, 3, 1–104 (1972). Results are expressed as percent inhibition, according to the formula: Inhibition (%)=(TuW$_{control}$−TuW$_{test}$)/TuW$_{control}$× 100%. The flank site of tumor implantation provides reproducible dose/response effects for a variety of chemotherapeutic agents, and the method of measurement (tumor diameter) is a reliable method for assessing tumor growth rates.

Administration of the compounds of this invention can be via any method which enables delivery of the compounds to the site of action (e.g., cancer cells). These methods include oral routes, intraduodenal routes, parenteral injection (including intravenous, subcutaneous, intramuscular, intravascular or infusion), topical administration, etc.

The amount of compound of this invention administered will, of course, be dependent on the subject being treated, on the severity of the affliction, on the manner of administration and on the judgment of the prescribing physician. However an effective dosage is in the range of approximately 0.1–100 mg/kg, preferably 1 to 35 mg/kg in single or divided doses. For an average 70 kg human, this would mount to 0.05 to 7 g/day, preferably 0.2 to 2.5 g/day. For topical administration (e.g., for psoriasis) a suitable formulation would include 0.01% to 5% of a compound of this invention, preferably 0.05% to 0.5%. Preferably the topical administration is applied directly to the site of affliction.

The pharmaceutical composition of the invention may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical compositions will include a conventional pharmaceutical carrier or excipient and a compound according to the invention as an active ingredient. In addition, it may include other medicinal or pharmaceutical agents, carriers, adjuvants, etc.

Pharmaceutical compositions for non-topical administration according to the invention may contain 0.1%–95% of the compound, preferably 1%–70%. In any event, the composition or formulation to be administered will contain a quantity of a compound according to the invention in an amount effective to alleviate or reduce the signs in the subject being treated, i.e., proliferative disorders, over the course of the treatment.

Exemplary parenteral administration forms include solutions or suspensions of a compound according to the invention Formula I in sterile aqueous solutions, for example aqueous propylene glycol or dextrose solutions are employed. Such dosage forms can be suitably buffered, if desired.

Suitable pharmaceutical carriers include inert diluents or fillers, water and various organic solvents. These pharmaceutical compositions can, if desired, contain additional ingredients such as flavorings, binders, excipients and the like. Thus for oral administration, tablets containing various excipients, such as citric acid can be employed, together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Preferred materials therefore include lactose or milk sugar and high molecular weight polyethylene glycols. When the aqueous suspensions or elixirs are desired for oral administration the essential active ingredient therein may be combined with various sweetening or flavoring agents, coloring matters or dyes and, if desired, emulsifying agents or suspending agents, together with diluents such as water, ethanol, propylene glycol, glycerin, or combinations thereof.

Methods of preparing various pharmaceutical compositions with a certain mount of active ingredient are known, or will be apparent in light of this disclosure, to those skilled in this art. For examples, see Remington's Pharmaceutical Sciences., Mack Publishing Company, Easter, Pa., 15th Edition (1975).

The anticancer treatment described above may be applied as a sole therapy or may involve, in addition to the quinazoline derivative of the invention, one or more other antitumor substances or radiotherapy. Such conjoint treatment may be achieved by way of the simultaneous, sequential, cyclic or separate dosing of the individual components of the treatment.

It should be understood that the invention is not limited to the particular embodiments shown and described herein, but that various changes and modifications may be made without departing from the spirit and scope of this novel concept as defined by the following claims.

EXAMPLES

Analytical reversed-phase HPLC (anal. RP18-HPLC) was performed by injecting samples dissolved in a water-miscible solvent onto a Perkin-Elmer Pecosphere® 3×3C cartridge column (3 mm×3 cm, C18; available from Perkin Elmer Corp., Norwalk, Conn. 06859) preceded by a Brownlee RP-8 Newguard precolumn (7 micron, 3.2 mm×15 mm, available from Applied Biosystems Inc. San Jose, Calif. 95134) both of which were previously equilibrated in pH4.50, 200 mM $NH_4$ OAc buffer. Samples were eluted using a linear gradient of 0–100% MeCN/pH4.50, 200 mM $NH_4$OAc over 10 minutes with a flow rate of 3.0 mL/min, Chromatograms were generated over the range 240–400 nm using a Diode array detector.

Gas Chromatography-Mass Spectrometry was carded out on a Hewlett Packard Instrument (5890 Series II) equipped with a 12 m HP-1 Column (200 μM i.d.). A temperature gradient from 133° C. (0–0.10 min.) to 310° C. at a heating rate of 18° C./min with an $He_{(g)}$ carrier was employed to separate components with peak detection through the use of a 5971 Series Mass Selective Detector.

Example 1

4-(6-Chloro-2,3-dihydro-indol-1-yl)-7,8-dihydro-[1,4]dioxino 2,3-g]guinazoline

To 6-chloroindoline (52 mg, 0.339 mmol) and pyridine (23.3 mg, 0.294 mmol) in i-PrOH (3 mL) was added 4-chloro-6,7-(ethylenedioxy)quinazoline (65 mg, 0.284 mmol). The mixture was heated to reflux under dry $N_{2(g)}$ for 16 hours and then concentrated in vacuo. The residue was partitioned between $CHCl_3$ and saturated aqueous $NaHCO_3$, and the organic phase was washed with brine, dried over $Na_2SO_{4(s)}$, and concentrated in vacuo. The residue was flash chromatographed on silica using 30% acetone/hexanes to afford 84 mg of 4-(6-chloro-2,3-dihydro-indol-1-yl)-7,8-dihydro-[1,4]dioxino [2,3-g]quinazoline as its free-base (M.P. 209°–211° C.; GC/MS: 339 ($M^+$); anal. RP18-HPLC RT: 5.02 min).

Example 2

4-6-Fluoro-2,3-dihydro-indol-1-yl)-6,7-dimethoxy-quinazoline

To 6-fluoroindoline (274 mg, 2.0 mmol) in dry i-PrOH (10mL) was added 4-chloro-6,7-dimethoxy-quinazoline (225 mg, 1.0 mmol). The mixture was refluxed for 16 hours under an atmosphere of dry $N_{2(g)}$ and then the solvent was removed in vacuo. The residue was partitioned between $CHCl_3$ and 1M NaOH, and the organic phase was washed with brine, dried over $Na2SO_{4(g)}$ and concentrated in vacuo. The residue (535 mg) was purified by flash chromatography on silica using 80%EtOAc/$CH_2Cl_2$ to yield 4-(6-fluoro-2,3-dihydro-indol-1-yl)-6,7-dimethoxyquinazoline as its free base (293 mg) (GC/MS: 325 ($M^+$); LC-MS: 326 ($MH^+$); anal. RP18-HPLC RT: 4.37 min.).

For conversion to its HCl salt this product (293 mg) was dissolved in minimal $CHCl_3$/$Et_2O$ and a 1M solution of HCl in $Et_2O$ (1.0 mL) was added dropwise with stirring. The resulting yellow HCl salt which precipitated was filtered out, washed with dry $Et_2O$ and pet. ether, and added in vacuo to constant mass (310 mg; M.P. 220° C. (dec)).

Example 3

4-(6-Chloro-2,3-dihydro-indol-1-yl)-6,7-dimethoxy-quinazoline

To 6-chloroindoline hydrochloride (1 00 mg, 0.526 mmol) and pyridine (0.957 mmol, 77 μL) in dry i-PrOH (8 mL) was added 4-chloro-6,7-dimethoxyquinazoline (107 mg, 0.478 mmol). The mixture was refluxed for 2 hours under an atmosphere of dry $N_{2(g)}$ and then the solvent was removed in vacuo. The residue was partitioned between $CHCl_3$ and 1M NaOH, and the organic phase was washed with brine, dried over $Na_2SO_{4(g)}$ and concentrated in vacuo. The residue (171 mg) was purified by flash chromatography on silica using 80%EtOAc/$CH_2Cl_2$ to yield 4-(6-chloro-2,3-dihydro-indol-1-yl)-6,7-dimethoxy-quinazoline as its free base (148 mg) (M.P. 229°–230° C.; LC-MS: 342 ($MH^+$); anal. RP18-HPLC RT: 4.38 min.).

Example 4

4-(2,3-Dihydro-indol-1-yl)-6,7-dimethoxy-quinazoline

Utilizing a procedure analogous to that described in Example 2, this product was prepared in 94% yield from indoline (2 eq.) and 4-chloro-6,7-dimethoxyquinazoline (1.0 eq) in i-PrOH. (M.P. 162°–163° C.; LC-MS: 308 ($MH^+$); anal. RP18-HPLC RT: 4.11 min.).

Example 5

6,7-Dimethoxy-4-(2-methyl-2,3-dihydro-indol-1-yl)-quinazoline

Utilizing a procedure analogous to that described in Example 1, this product was prepared in 91% yield from 2-methyl-indoline (1.1 eq.) and 4-chloro-6,7-dimethoxyquinazoline (1.0 eq) in i-PrOH. (M.P. 154°–156.5° C.; GC-MS: 321 ($M^+$); anal. RP18-HPLC RT: 4.93 min.).

Example 6

4-(4-Chloro-2,3-dihydro-indol-1-yl)-6,7-dimethoxy-quinazoline

Utilizing a procedure analogous to that described in Example 2, this product was prepared in 92% yield from 4-chloro-indoline (2 eq.) and 4-chloro-6,7-dimethoxyquinazoline (1.0 eq) in i-PrOH. (M.P. 172°–179° C. (dec); LC-MS: 342 ($MH^+$); anal. RP18-HPLC RT: 4.60 min.).

Example 7

4-(3,4-Dihydro-2H-quinolin-1-yl)-6,7-dimethoxy-quinazoline

Utilizing a procedure analogous to that described in Example 2, this product was prepared in 91% yield from 1,2,3,4-tetrahydroquinoline (2 eq.) and 4-chloro-6,7- dimethoxy-quinazoline (1.0 eq) in i-PrOH. (M.P. 130°–131° C.; LC-MS: 322 (MH⁺); anal. RP18-HPLC RT: 4.08 min.).

Example 8

6,7-Dimethoxy-4-(6-methyl-3,4-dihydro-2H-quinolin-1-yl)-quinazoline

Utilizing a procedure analogous to that described in Example 2, this product was prepared in 94% yield from 6-methyl-1,2,3,4-tetrahydroquinoline (2 eq.) and 4-chloro-6,7-dimethoxy-quinazoline (1.0 eq) in i-PrOH. (M.P. 147°–148° C.; LC-MS: 336 (MH⁺); anal. RP18-HPLC RT: 4.51 min.).

Example 9

6,7-Dimethoxy-4-(7-trifluoromethyl-3,4-dihydro-2H-quinolin-1-yl)-quinazoline Utilizing a procedure analogous to that described in Example 2, this product was prepared in 66% recrystallized yield (from CHCl₃/hexane) from 6-trifluoromethyl-1,2,3,4-tetrahydroquinoline (2 eq.) and 4-chloro-6,7-dimethoxy-quinazoline (1.0 eq) in i-PrOH. (M.P. 184°–185° C.; LC-MS: 390 (MH⁺); anal. RP18-HPLC RT: 5.10 min.).

Example 10

4-6-Chloro-2,3-dihydro-indol-1-yl)-6,7-diethoxy-quinazoline

Utilizing a procedure analogous to that described in Example 1, this product was prepared in 99% yield from 6-chloro-indoline (1.1 eq.) and 4-chloro-6,7-diethoxyquinazoline (1.0 eq) in i-PrOH. (M.P. 159°–163° C.; GC-MS: 369 (M⁺); anal. RP18-HPLC RT: 5.25 min.).

Example 11

7-Butoxy-4-(6-chloro-2,3-dihydro-indol-1-yl)-6-methoxy-quinazoline

Utilizing a procedure analogous to that described in Example 1, this product was prepared in 43% yield from 6-chloro-indoline (1.1 eq.) and 7-butoxy-4-chloro-6-methoxy-quinazoline (1.0 eq) in i-PrOH. (M.P. 126°–132° C.; GC-MS: 383 (M⁺); anal. RP18-HPLC RT: 6.22 min.).

Example 12

6,7-Dimethoxy-4-(6-methyl-2,3-dihydro-indol-1-yl)-quinazoline hydrochloride

Utilizing a procedure analogous to that described in Example 1, this product was prepared in 88% yield from 6-methyl-indoline (1.1 eq.) and 4-chloro-6,7-dimethoxy-quinazoline (1.0 eq) in i-PrOH. The HCl salt was generated from the purified free base according to the procedure given in Example 2 (M.P. 231°–232° C.; LC-MS: 322 (MH⁺); anal. RP18-HPLC RT: 4.32 min.).

Example 13

6,7-Dimethoxy-4-(4-methyl-2,3-dihydro-indol-1-yl)-quinazoline

Utilizing a procedure analogous to that described in Example 1, this product was prepared in 94% yield from 4-methyl-indoline (1.1 eq.) and 4-chloro-6,7-dimethoxy-quinazoline (1.0 eq) in i-PrOH. (M.P. 174°–175° C.; LC-MS: 322 (MH⁺); anal. RP18-HPLC RT: 4.85 min.).

Examples 14 & 15

6,7-Dimethoxy-4-(cis-2,3-dimethyl-2,3-dihydro-indol-1-yl)-quinazoline and 6,7-Dimethoxy-4-(trans-2,3-dimethyl-2,3-dihydro-indol-1-yl)-quinazoline These products were obtained as racemates following flash chromatography on silica in 55–65% EtOAc/hexanes in 65% & 15% yield, respectively, when prepared from a commercial mixture of cis/trans-2,3-dimethyl-indoline (1.1 eq.) and 4-chloro-6,7-dimethoxy-quinazoline (1.0 eq) in i-PrOH utilizing a procedure analogous to that described in Example 1. For the cis-isomer: M.P. 174°–175° C.; LC-MS: 336 (MH⁺); anal. RP18-HPLC RT: 5.15 min.; For the trans-isomer: LC-MS: 336 (MH⁺); anal. RP18-HPLC RT: 4.83 min.

Example 16

4-(6-Iodo-2,3-dihydro-indol-1-yl)-6,7-dimethoxy-quinazoline hydrochloride

Utilizing a procedure analogous to that described in Example 1, this product was prepared in 78% yield from 6-iodo-indoline (1.1 eq.) and 4-chloro-6,7-dimethoxy-quinazoline (1.0 eq) in i-PrOH. The HCl salt was generated from the purified free base according to the procedure given in Example 2 (M.P. >230° C.; GC/MS: 433 (M⁺); anal. RP18-HPLC RT: 5.20 min.).

Example 17

4-(5-Fluoro-2,3-dihydro-indol-1-yl)-6,7-dimethoxy-quinazoline

Utilizing a procedure analogous to that described in Example 1, this product was prepared in 81% yield from 5-fluoro-indoline (1.1 eq.) and 4-chloro-6,7-dimethoxy-quinazoline (1.0 eq) in i-PrOH. (M.P. 190°–191° C.; LC-MS: 326 (MH⁺); anal. RP18-HPLC RT: 4.40 min.).

Example 18

4-(6-Chloro-2,3-dihydro-indol-1-yl)-6,7,8-trimethoxy-quinazoline

Utilizing a procedure analogous to that described in Example 1, this product was prepared in 20% yield from 6-chloro-indoline (1.1 eq.) and 4-chloro-6,7,8-trimethoxy-quinazoline (1.0 eq) in i-PrOH. (M.P. 139°–143° C.; GC/MS: 371 (M⁺); anal. RP18-HPLC RT: 4.70 min.).

Example 19

4-(6-Benzyloxy-2,3-dihydro-indol-1-yl)-6,7-dimethoxy-quinazoline hydrochloride Utilizing a procedure analogous to that described in Example 1, this product was prepared in 80% yield from 6-benzyloxy-indoline (1.1 eq.) and 4-chloro-6,7-dimethoxy-quinazoline (1.0 eq) in i-PrOH. The HCl salt was generated from the purified free base according to the procedure given in Example 2. (M.P. 249°–250° C.(dec); LC-MS: 414 (MH⁺); anal. RP18-HPLC RT: 5.01 min.).

Example 20

6,7-Dimethoxy-4-(6-methoxy-2,3-dihydro-indol-1-yl)-quinazoline hydrochloride Utilizing a procedure analogous to that described in Example 1, this product was prepared in 91% yield from 6-methoxy-indoline (1.1 eq.) and 4-chloro-6,7-dimethoxy-quinazoline (1.0 eq) in i-PrOH. The HCl salt was generated from the purified free base according to a procedure analogous to that given in Example 2. (M.P. 246°–247° C.(dec); LC-MS: 338 (MH$^+$); anal. RP18-HPLC RT: 4.27 min.).

Example 21

4-(6-Bromo-2,3-dihydro-indol-1-yl)-6,7-dimethoxy-quinazoline hydrochloride

Utilizing a procedure analogous to that described in Example 1, this product was prepared in 88% yield from 6-bromo-indoline (1.1 eq.) and 4-chloro-6,7-dimethoxy-quinazoline (1.0 eq) in i-PrOH. The HCl salt was generated from the purified free base according to a procedure analogous to that given in Example 2. (M.P. 245°–248° C.(dec); LC-MS: 386, 388 (MH$^+$); anal. RP18-HPLC RT: 4.95 min.).

Example 22

4-(5-Chloro-2,3-dihydro-indol-1-yl)-6,7-dimethoxy-quinazoline

Utilizing a procedure analogous to that described in Example 1, this product was prepared in 92% yield from 5-chloro-indoline (1.1 eq.) and 4-chloro-6,7-dimethoxy-quinazoline (1.0 eq) in i-PrOH. (M.P. 190°14 191° C.; GC/MS: 3.41 (M$^+$); anal. RP18-HPLC RT: 4.58 min.).

Example 23

6,7-Dimethoxy-4-(5-methyl-2,3-dihydro-indol-1-yl)-quinazoline

Utilizing a procedure analogous to that described in Example 1, this product was prepared in 94% yield from 5-methyl-indoline (1.1 eq.) and 4-chloro-6,7-dimethoxy-quinazoline (1.0 eq) in i-PrOH. (M.P. 180°–181° C.; GC/MS: 321 (M$^+$); anal. RP18-HPLC RT: 4.37 min.).

Example 24

1-(6,7-Dimethoxy-quinazolin-4-yl)-2,3-dihydro-1H-indole-2-carboxylic acid methyl ester DL-Indoline-2-carboxylic acid methyl ester (0.806g, 4.55 mmol) and pyridine (0.236 mL, 4.51 mmol) were added to a solution of 4-chloro-6,7-dimethoxy-quinazoline (1.01 g, 4.50 mmol)in DMF (10 mL) and the mixture was heated to 80° C. for 4.5 hours. The product was isolated in 87% yield following extractive workup and flash chromatography as in Example 1. (M.P. 186°–189.5° C.; LC-MS: 366 (MH$^+$); anal. RP18-HPLC RT: 4.28 min.).

Example 25

4-(3,4-Dihydro-2H-quinolin-1-yl)-6-methoxy-quinazoline

Utilizing a procedure analogous to that described in Example 2, this product was prepared in 59% yield from 1,2,3,4-tetrahydroquinoline (2 eq.) and 4-chloro-6-methoxy-quinazoline (1.0 eq) in EtOH. (M.P. 98° C.; LC-MS: 292 (MH$^+$).

Example 26

6,7-Dimethoxy-4-(6-nitro-2,3-dihydro-indol-1-yl)-quinazoline

Utilizing a procedure analogous to that described in Example 1, this product was prepared in 91% yield from 6-nitro-indoline (1 eq.) and 4-chloro-6,7-dimethoxy-quinazoline (1.0 eq) in i-PrOH. (M.P. 275° C. (dec); GC-MS: 352 (M$^+$); anal. RP18-HPLC RT: 4.30 min.).

Example 27

4-(6-Bromo-5-fluoro-2,3-dihydro-indol-1-yl)-6,7-dimethoxy-quinazoline hydrochloride salt Utilizing a procedure analogous to that described in Example 1, this product was prepared in 68% yield from 5-fluoro-6-bromo-indoline (1.1 eq.) and 4-chloro-6,7-dimethoxy-quinazoline (1.0 eq) in i-PrOH. (M.P. 258° C. (dec); LC-MS: 404, 406 (MH$^+$); anal. RP18-HPLC RT: 5.06 min.).

Example 28

6,7-Dimethoxy-4-(7-methyl-2,3-dihydro-indol-1-yl)-quinazoline

Utilizing a procedure analogous to that described in Example 24, this product was prepared in 65% yield from 7-methyl-indoline (1 eq.), pyridine (2 eq.) and 4-chloro-6,7-dimethoxy-quinazoline (1.0 eq) in DMF. (M.P. 146°–147° C.; GC-MS: 321 (M$^+$); anal. RP18-HPLC RT: 4.41 min.).

Example 29

[1-(6,7-Dimethoxy-quinazolin-4-yl)-2,3-dihydro-1H-indol-2-yl]-methanol

Utilizing a procedure analogous to that described in Example 1, this product was prepared in 57% yield from 2-hydroxymethyl-indoline (1 eq.) and 4-chloro-6,7-dimethoxy-quinazoline (1.0 eq) in i-PrOH. (M.P. 145.5°–147° C.; LC-MS: 338 (MH$^+$); anal. RP18-HPLC RT: 4.03 min.).

Example 30

1-(6,7-Dimethoxy-quinazolin-4-yl)-2,3-dihydro-1H-indol-6-ylamine 6,7-Dimethoxy-4-(6-nitro-2,3-dihydro-indol-1-yl)-quinazoline (0.50 g, 1.42 mmol; from Example 26) in MeOH (10 mL) with conc. HCl (1 mL) was hydrogenated for 18 hours under 45 psi of H$_{2(g)}$ in the presence of 10% Pd-C (105 mg). Following filtration through a pad of Celite and concentration of the filtrate in vacuo, the residue was taken up in 10% i-PrOH/CHCl$_3$ and the organic phase washed successively with saturated NaHCO$_3$, 0.1M disodium EDTA, and brine. The organic solution was added over Na$_2$SO$_{4(s)}$, filtered and concentrated in vacuo to afford the product as a yellow solid (423 mg; M.P. 215°–217.5° C.; LC-MS: 323 (MH$^+$); anal. RP-HPLC RT: 3.10 min).

Example 31

4-(6-Isothiocyanato-2,3-dihydro-indol-1-yl)-6,7-dimethoxy-quinazoline

To a solution of thiocarbonyl diimidazole (90 mg, 0.505 mmol) in CHCl$_3$ (1 mL) was added dropwise a solution of 1-(6,7-dimethoxy-quinazolin-4-yl)-2,3-dihydro-1H-indol-6-ylamine (163 mg, 0.606 mmol; from Example 30) in CH$_3$CN (8 mL) at 5°–10° C. over 2 hours. After stirring 4 hours at 5° C. the solvent was removed in vacuo and the residue was flash chromatographed on silica (1% MeOH/CHCl$_3$) to afford 115 mg of the isothiocyanate product (M.P. 214°–215° C.; GC-MS: 364 (M$^+$); anal. RP18-HPLC RT: 5.60 min.).

Example 32

6,7-Dimethoxy-4-(6-pyrrol-1-yl-2,3-dihydro-indol-1-yl)-quinazoline

To 1-(6,7-Dimethoxy-quinazolin-4-yl)-2,3-dihydro-1H-indol-6-ylamine (155 mg, 0.481 mmol, from Example 30) in glacial acetic acid (4 mL) was added 1,4-dimethoxy-tetrahydrofuran (72.3 μL, 0.558 mmol). The mixture was heated to 90° C. under dry $N_{2(g)}$ for 4 hours and concentrated in vacuo. The residue was dissolved in $CHCl_3$ and washed with saturated aqueous $NaHCO_3$ (2×), and brine and the organic phase was dried over $MgSO_{4(s)}$, filtered and concentrated in vacuo. The residue was chromatographed on silica (50% acetone/hexanes) to afford 71 mg of the 6-pyrrolyl derivative. (M.P. 185°–186° C.; GC-MS: 372 ($M^+$); anal. RP18-HPLC RT: 4.60 min.).

Examples 33 & 34

6,7-Dimethoxy-4-(trans-octahydro-indol-1-yl)-quinazoline & 6,7-Dimethoxy-4-(cis-octahydro-indol-1-yl)-quinazoline Utilizing a procedure analogous to that described in Example 24, the title products were prepared from cis/trans-perhydroindole (1.1 eq.), triethylamine (1.1 eq.) and 4-chloro-6,7-dimethoxy-quinazoline (1.0 eq) in DMF. Isomers were resolved on silica using EtOAc as the eluant to afford 16% of the trans-isomer (M.P. 130°–131° C.; LC-MS: 3.14 ($MH^+$); anal. RP18-HPLC RT: 4.05 min.) and 46% of the cis-isomer (M.P. 123°–124° C.; LC-MS: 314 ($MH^+$); anal. RP18-HPLC RT: 3.89 min.).

Example 35

4-(6-Bromo-7-methyl-2,3-dihydro-indol-1-yl)-6,7-dimethoxy-quinazoline

Utilizing a procedure analogous to that described in Example 24, this product was prepared in 93% yield from 5-bromo-7-methyl-indoline (1.1 eq.), and 4-chloro-6,7-dimethoxy-quinazoline (1.0 eq) in DMF. (M.P. 240°–242° C.; LC-MS: 400, 402 ($MH^+$); anal. RP18-HPLC RT: 5.13 min.). The hydrochloride salt was produced using procedures analogous to that as described for Example 2: M.P. 243°–244° C..

Example 36

4-(4-Bromo-7-methyl-2,3-dihydro-indol-1-yl)-6,7-dimethoxy-quinazoline

Utilizing a procedure analogous to that described in Example 24, this product was prepared in 70% yield from 4-bromo-7-methyl-indoline (1.1 eq.), and 4-chloro-6,7-dimethoxy-quinazoline (1.0 eq) in DMF. (M.P. 223°–225° C.; LC-MS: 400, 402 ($MH^+$); anal. RP18-HPLC RT: 5.23 min.).

Example 37

4-6-dihydro-indol-1-yl)-6,7-dimethoxy-quinazoline

Utilizing a procedure analogous to that described in Example 1, this product was prepared in 53% yield from 6-n-butyl-indoline (1.1 eq.), and 4-chloro-6,7-dimethoxy-quinazoline (1.0 eq) in i-PrOH. (M.P. 130°–131° C.; GC-MS: 363 ($M^+$); anal. RP18-HPLC RT: 5.41 min.).

Example 38

6,7-Dimethoxy-4-(6-phenyl-2,3-dihydro-indol-1-yl)-quinazoline

Utilizing a procedure analogous to that described in Example 1, this product was prepared in 61% yield from 6-phenyl-indoline (1.1 eq.), and 4-chloro-6,7- dimethoxy-quinazoline (1.0 eq) in i-PrOH. (M.P. 175°–177° C.; GC-MS: 383 ($M^+$); anal. RP18-HPLC RT: 6.03min.).

Example 39

5-(6,7-Dimethoxy-quinazolin-4-yl)-6,7-dihydro-5H-[1,3]dioxolo[4,5-f]indole

Utilizing a procedure analogous to that described in Example 1, this product was prepared in 93% yield from 6,7-dihydro-5H-[1,3]dioxolo[4,5-f]indole (1.1 eq.), and 4-chloro-6,7-dimethoxy-quinazoline (1.0 eq) in i-PrOH. (M.P. 225°–228° C. (dec); LC-MS: 352 ($MH^+$); anal. RP18-HPLC RT: 3.91 min.).

Example 40

4-(6-Isopropyl-2,3-dihydro-indol-1-yl)-6,7-dimethoxy-quinazoline

Utilizing a procedure analogous to that described in Example 1, this product was prepared in 43% yield from 6-isopropyl-indoline (1.1 eq.), and 4-chloro-6,7-dimethoxy-quinazoline (1.0 eq) in i-PrOH. (M.P. 128°–129° C.; LC-MS: 350 ($MH^+$); anal. RP18-HPLC RT: 5.51 min.).

Example 41

6,7-Dimethoxy-4-(6-propyl-2,3-dihydro-indol-1-yl)-quinazoline

Utilizing a procedure analogous to that described in Example 1, this product was prepared in 43% yield from 6-propyl-indoline (1.1 eq.), and 4-chloro-6,7-dimethoxy-quinazoline (1.0 eq) in i-PrOH.(M.P. 140°–141° C.; LC-MS: 350 ($MH^+$); anal. RP18-HPLC RT: 5.73 min.).

Example 42

4-(6-Azido-2,3-dihydro-indol-1-yl)-6,7-dimethoxy-quinazoline

To 1-(6,7-dimethoxy-quinazolin-4-yl)-2,3-dihydro-1H-indol-6-ylamine (104 mg, 0.323 mmol; from Example 30) in 80% acetic acid/$H_2O$ (8 mL) was added $NaNO_2$ (35 mg, 0.35 mmol) in $H_2O$(200 μL) at 5° C. After stirring 10 min. at 5° C. a solution of $NaN_3$ (22mg, 0.34 mmol) in $H_2O$(200 μL) was added and the mixture was allowed to warm to 22° C. and stirred for 1 hour. Following the removal of solvents by lyophilization the residue was dissolved in EtOAc and washed with saturated aqueous $NaHCO_3$ (2×), and brine, and the organic phase was dried over $MgSO_{4(s)}$, filtered and concentrated in vacuo. The residue was chromatographed on silica (2% $MeOH/CHCl_3$) to afford 72 mg of the azide. (M.P. 184°–186° C. (dec); LC-MS: 349 ($MH^+$); anal. RP18-HPLC RT: 4.70 min.).

Example 43

[1-(6,7-Dimethoxy-quinazolin-4-yl)-2,3-dihydro-1H-indol-5-yl]-(1-methyl-heptyl)-amine Utilizing a procedure analogous to that described in Example 1, this product was prepared in 96% yield from [2,3-dihydro-1H-indol-5-yl]-(1-methyl-heptyl)-amine (1.1 eq.), and 4-chloro-6,7-dimethoxy-quinazoline (1.0 eq) in i-PrOH. (M.P. 61°–63° C.; GC-MS: 434 ($M^+$); anal. RP18-HPLC RT: 6.91 min.).

Example 44

6,7-Dimethoxy-4-(5-methoxy-2,3-dihydro-indol-1-yl)-quinazoline methanesulfonate salt Utilizing a procedure analogous to that described in Example 1, this product was prepared in 95% yield from 5-methoxy-indoline (1.1 eq.), and 4-chloro-6,7-dimethoxy-quinazoline (1.0 eq) in i-PrOH. The free-base obtained following column chromatography on silica (45% acetone/hexanes) was dissolved in minimal $CH_2Cl_2$ and treated with 1 eq. of methanesulfonic acid in $CH_2Cl_2$ followed by dilution with several volumes of ether to precipitate the mesylate salt which was filtered and added in vacuo. (M.P. 285°–292° C. (dec); LC-MS: 338 (MH+); anal. RP18-HPLC RT: 3.82 min.).

Example 45

4-(5-Benzyloxy-2,3-dihydro-indol-1-yl)-6,7-dimethoxy-quinazoline

Utilizing a procedure analogous to that described in Example 1, this product was prepared in 90% yield from 5-benzyloxy-indoline (1.1 eq.), and 4-chloro-6,7-dimethoxy-quinazoline (1.0 eq) in i-PrOH. (M.P. 181°–182° C.; LC-MS: 415 (MH$^+$); anal. RP18-HPLC RT: 4.78 min.).

Example 46

6,7-Dimethoxy-4-(6-pyrrolidin-1-yl-2,3-dihydro-indol-1-yl)-quinazoline

To 1-(6,7-dimethoxy-quinazolin-4-yl)-2,3-dihydro-1H-indol-6-ylamine (103 mg, 0.320 mmol; from Example 30) in DMF (4 mL) was added 1,4-dibromo-butane (42 µL, 0.352 mmol) and pyridine (34 µL, 0.64 mmol) and the mixture was heated to 110° C. for 36 hours under $N_{2(g)}$. The mixture was diluted with saturated aqueous $NaHCO_3$ and extracted with EtOAc/Et$_2$O (1:1) and the organic phase was washed with water and brine, dried over $Na_2SO_{4(s)}$, filtered and concentrated in vacuo. The residue was chromatographed on silica (4% MeOH/CHCl$_3$) to afford 20 mg of product. (M.P. 198°–205° C. (dec); GC-MS: 376 (M$^+$); anal. RP18-HPLC RT: 5.05 min.).

Example 47

4-(6-Chloro-5-fluoro-2,3-dihydro-indol-1-yl)-6,7-dimethoxy-quinazoline methanesulfonate salt 6-Chloro-5-fluoro-indoline (157 mg, 0.915 mmol), pyridine (48 µL), and 4-chloro-6,7-dimethoxy-quinazoline (210 mg, 0.895 mmol) were heated to 120° C. in N-methyl-pyrrolidin-2-one (2 mL) under $N_{2(g)}$ for 36 hours. The mixture was partitioned between EtOAc and saturated aqueous $NaHCO_3$, and the organic phase was washed several times with water and brine, dried over $MgSO_{4(g)}$, filtered and concentrated in vacuo. The residue was flash chromatographed on silica using 40% acetone/hexanes to elute the product (90 mg) which was converted to the methanesulfonate salt as described in Example 44. (M.P. 261°–264° C.; LC-MS: 360 (MH$^+$); anal. RP18-HPLC RT: 4.31 min.).

Example 48

1-(6,7-Dimethoxy-quinazolin-4-yl)-2,3-dihydro-1H-indol-5-ol methanesulfonate salt Utilizing a procedure analogous to that described in Example 1 (with conversion to the methanesulfonate salt analogous to that described in Example 44), this product was prepared in 90% yield from 5-hydroxy-indoline (1.1 eq.), and 4-chloro-6,7-dimethoxy-quinazoline (1.0 eq) in i-PrOH. (M.P. 245°–250° C. (dec); LC-MS: 324 (MH$^+$); anal. RP18-HPLC RT: 2.76 min.).

Example 49

1-(6,7-Dimethoxy-quinazolin-4-yl)-6-methyl-2,3-dihydro-1H-indol-5-ol methanesulfonate salt Utilizing a procedure analogous to that described in Example 1 (with conversion to the methanesulfonate salt analogous to that described in Example 44), this product was prepared in 45% yield from 5-hydroxy-6-methyl-indoline (1.1 eq.), and 4-chloro-6,7-dimethoxy-quinazoline (1.0 eq) in i-PrOH. (For Free base: M.P. 230° C.; For salt: M.P. 290° C. (dec); LC-MS: 338 (MH$^+$); anal. RP18-HPLC RT: 3.11 min.).

Example 50

4-(6,7-Dimethyl-2,3-dihydro-indol-1-yl)-6,7-dimethoxy-quinazoline methanesulfonate salt Utilizing a procedure analogous to that described in Example 47 (with conversion to the methanesulfonate salt analogous to that described in Example 44), this product was prepared in 92% yield from 6,7-dimethyl-indoline (1.1 eq.), and 4-chloro-6,7-dimethoxy-quinazoline (1.0 eq) in N-methyl-pyrrolidin-2-one. (M.P. 232°–237° C.; GC-MS: 335 (M$^+$); anal. RP18-HPLC RT: 4.44 min.).

Example 51

1-(6,7-Dimethoxy-quinazolin-4-yl)-2,3,4,5-tetrahydro-1H-benzo[b]azepine methanesulfonate salt Utilizing a procedure analogous to that described in Example 47 (with conversion to the methanesulfonate salt analogous to that described in Example 44), this product was prepared in 92% yield from 2,3,4,5-tetrahydro-1H-benzo[b]azepine (1.1 eq,), and 4-chloro-6,7-dimethoxy-quinazoline (1.0 eq) in N-methyl-pyrrolidinone. (M.P. 218.2°–218.6° C.; LC-MS: 336 (MH$^+$); anal. RP18-HPLC RT: 4.46 min.).

Example 52

6,7-Dimethoxy-4-(5-nitro-2,3-dihydro-indol-1-yl)-quinazoline

Utilizing a procedure analogous to that described in Example 47, the adduct from 5-nitro-indoline (1.1 eq.), and 4-chloro-6,7-dimethoxy-quinazoline (1.0 eq) in N-methyl-pyrrolidinone was isolated in 42% yield (M.P. 245°–249° C. (dec); LC-MS: 353 (MH+); anal. RP18-HPLC RT: 3.95 min.).

Example 53

4-(5-Azido-2,3-dihydro-indol-1-yl)-6,7-dimethoxy-quinazoline

A solution of 1-(6,7-dimethoxy-quinazolin-4-yl)-2,3-dihydro-1H-indol-5-ylamine (155 mg, 0.481 mmol; from Example 83 as the free-base) in 80% AcOH/H$_2$O (10 mL) was treated using procedures analogous to that described in Example 42 to afford the azide derivative in 47% isolated yield. (M.P. 159°–165° C. (dec); LC-MS: 349 (MH$^+$); anal. RP18-HPLC RT: 4.93 min.).

Example 54

6-Chloro-1-(6,7-dimethoxy-quinazolin-4-yl)-2,3-dihydro-1H-indol-5-ol methanesulfonate salt Utilizing a procedure analogous to that described in Example B (with conversion to the methanesulfonate salt analogous to that described in Example 44), this product was prepared in 49% yield from 6-chloro-5-hydroxy-indoline (1.1 eq.), and 4-chloro-6,7-dimethoxy-quinazoline (1.0 eq) in i-PrOH. (M.P. 268°–275° C.; LC-MS: 358 (MH$^+$); anal. RP18-HPLC RT: 3.45 min.).

Example 55

1-(6,7-Dimethoxy-quinazolin-4-yl)-7-methyl-2,3-dihydro-1H-indol-5-ol methanesulfonate salt Utilizing a procedure analogous to that described in Example 1 (with conversion to the methanesulfonate salt analogous to that described in Example 44), this product was prepared in 73% yield from 5-hydroxy-7-methyl-indoline (1.1 eq.), and 4-chloro-6,7-dimethoxy-quinazoline (1.0 eq) in i-PrOH. (M.P. 145°–146° C. (dec); LC-MS: 338 (MH$^+$); anal. RP18-HPLC RT: 3.20 min.).

Example 56

1-(6,7-Dimethoxy-quinazolin-4-yl)-6,7-dimethyl-2,3-dihydro-1H-indol-5-ol hydrochloride salt Utilizing a procedure analogous to that described in Example 47 this product (with conversion to the HCl salt as outlined for Example 2) was prepared in 40% yield from 5-hydroxy-6,7-dimethyl-indoline (1.1 eq.), and 4-chloro-6,7-dimethoxy-quinazoline (1.0 eq) in N-methyl-pyrrolidinone. (M.P. 207°–209° C. (dec); LC-MS: 352 (MH$^+$); anal. RP18-HPLC RT: 3.48 min.).

Example 57

4-(5,7-Dichloro-2,3-dihydro-indol-1-yl)-6,7-dimethoxy-quinazoline acetate salt

Utilizing a procedure analogous to that described in Example 47 this product was prepared in 16% yield from 5,7-dichloro-indoline (1.1 eq.), and 4-chloro-6,7-dimethoxy-quinazoline (1.0 eq) in N-methyl-pyrrolidinone. The product was isolated as its acetate salt by preparative RP(C18)-HPLC using a gradient of 10 to 60% CH$_3$CN/ pH4.5, 50 mM NH$_4$OAc followed by lyophilization. (M.P. 228°–232.5° C.; LC-MS: 376 (MH$^+$); anal. RP18-HPLC RT: 5.20 min.).

Example 58

4-(6-Chloro-5-nitro-2,3-dihydro-indol-1-yl)-6,7-dimethoxy-quinazoline

Utilizing a procedure analogous to that described in Example 47 this product was prepared in 24% yield from 6-chloro-5-nitro-indoline (1.1 eq.), and 4-chloro-6,7-dimethoxy-quinazoline (1.0 eq) in N-methyl-pyrrolidinone. (M.P. 276°–278° C.; LC-MS: 387 (MH$^+$); anal. RP18-HPLC RT: 4.48 min.).

Example 59

6-Chloro-1-(6,7-dimethoxy-quinazolin-4-yl)-2,3-dihydro-1H-indol-5-ylamine hydrochloride salt To 4-(6-chloro-5-nitro-2,3-dihydro-indol-1-yl)-6,7-dimethoxy-quinazoline (150 mg, 0.386 mmol; from Example 58) in THF (5 mL) with 10% Pd-C (21 mg) at 40° C. was added NaH$_2$PO$_2$.H$_2$O (490 mg, 3.86 mmol) in H$_2$O (0.5 mL) dropwise over 20 minutes. The mixture was stirred at 40° C. for 5 hours. Following removal of the catalyst by filtration through Celite, and concentration in vacuo the residue was dissolved in 10% .i-PrOH/CHCl$_3$, washed with saturated aqueous NaHCO$_3$, and brine, dried over Na$_2$SO$_4$ (s), filtered and concentrated in vacuo to afford 121 mg (90%) of product which was converted to the HCl salt as outlined for Example 2. (M.P. 223°–228° C.; LC-MS: 367 (MH$^+$); anal. RP18-HPLC RT: 3.68 min.).

Example 60

4-(4-Bromo-7-methyl-2,3-dihydro-indol-1-yl)-7-methoxy-quinazoline

Utilizing a procedure analogous to that described in Example 1, this product was prepared in 69% yield from 4-bromo-7-methyl-indoline (1.1 eq.), and 4-chloro-7-methoxy-quinazoline (1.0 eq) in i-PrOH. (M.P. 134°–135° C.; LC-MS: 370, 372 (MH$^+$); anal. RP18-HPLC RT: 5.60 min.).

Example 61

4-(6-Bromo-7-methyl-2,3-dihydro-indol-1-yl)-7-methoxy-quinazoline hydrochloride salt Utilizing a procedure analogous to that described in Example 1 (with conversion to the HCl salt as outlined for Example 2), this product was prepared in 49% yield from 6-bromo-7-methyl-indoline (1.1 eq.), and 4-chloro-7-methoxy-quinazoline (1.0 eq) in i-PrOH. (M.P. 200°–205° C. (dec); LC-MS: 370, 372 (MH$^+$); anal. RP18-HPLC RT: 5.76 min.).

Example 62

7-Methoxy-4-(7-methyl-2,3-dihydro-indol-1-yl)-quinazoline

Utilizing a procedure analogous to that described in Example 1 this product was prepared in 79% yield from 7-methyl-indoline (1.1 eq.), and 4-chloro-7-methoxy-quinazoline (1.0 eq) in i-PrOH. (M.P. 157°–160° C. (dec); LC-MS: 292 (MH$^+$); anal. RP18-HPLC RT: 4.30 min.).

Example 63

4-(6-Bromo-5-fluoro-2,3-dihydro-indol-1-yl)-7-methoxy-quinazoline hydrochloride salt Utilizing a procedure analogous to that described in Example 1 (with conversion to the HCl salt as outlined for Example 2), this product was prepared in 74% yield from 6-bromo-5-fluoro-indoline (1.1 eq.), and 4-chloro-7-methoxy-quinazoline (1.0 eq) in i-PrOH. (M.P. 252°–252° C.; LC-MS: 374, 376 (MH$^+$); anal. RP18-HPLC RT: 5.26 min.).

Example 64

4-(6-Chloro-2,3-dihydro-indol-1-yl)-7-methoxy-quinazoline hydrochloride salt

Utilizing a procedure analogous to that described in Example 1 (with conversion to the HCl salt as outlined for Example 2), this product was prepared in 82% yield from 6-chloro-indoline (1.1 eq.), and 4-chloro-7-methoxy-quinazoline (1.0 eq) in i-PrOH. (M.P. of free-base: 140°–141° C.; For HCl salt: M.P. 232°–233° C.; LC-MS: 312 (MH$^+$); anal. RP18-HPLC RT: 5.68 min.).

Example 65

4-(6-Chloro-2,3-dihydro-indol-1-yl)-quinazolin-7-ol 4-(6-Chloro-2,3-dihydro-indol-1-yl)-7-methoxy-quinazoline (7.596 g, 24.4 mmol; free-base from Example 64) was added in several portions over 5 minutes to molten pyridine hydrochloride (85 g) at 170° C. The stoppered mixture was heated 75 minutes and then poured into ice/ water (~600 mL). The precipitated solid was filtered, dissolved in 10% i-PrOH/CHCl$_3$, and the organic solution was washed with saturated aqueous NaHCO$_3$ and brine, dried over Na$_2$SO$_{4(s)}$, filtered and concentrated in vacuo to afford 3.14 g. of product. (M.P. 270°–280° C. (dec); LC-MS: 298 (MH$^+$); anal. RP18-HPLC RT: 4.00 min.).

Example 66

4-(6-Chloro-2,3-dihydro-indol-1-yl)-7-(2-methoxy-ethoxy)-quinazoline hydrochloride salt To 4-(6-chloro-2,3-dihydro-indol-1-yl)-quinazolin-7-ol (125 mg, 0.42 mmol; from Example 65) in DMF (2 mL) was added H$_2$O (50 μL), K$_2$CO$_3$(s) (116 mg, 0.84 mmol), and tetramethylammonium hydroxide pentahydrate (15 mg, 0.08 mmol) followed by 2-bromoethyl methyl ether (43 μL, 0.46 mmol). The mixture was stirred at 50° C. under N$_{2(g)}$ for 24 hours before another aliquot (43 μL) of 2-bromoethyl methyl ether was added. Stirring at 50° C. was continued for another 36 hours before extractive workup and chromatography analogous to that described in Example 1 followed by conversion to the HCl salt as outlined for Example 2 afforded 91 mg (61%) of product. (M.P. 213°–216° C. (dec); LC-MS: 356 (MH$^+$); anal. RP18-HPLC RT: 4.73 min.).

Example 67

2-[4-(6-Chloro-2,3-dihydro-indol-1-yl)-quinazolin-7-yloxy]-ethanol hydrochloride salt To 4-(6-chloro-2,3-dihydro-indol-1-yl)-quinazolin-7-ol (125 mg, 0.42 mmol; from Example 65) in DMF (2 mL) was added H$_2$O (50 μL), K$_2$CO$_3$(s) (116 mg, 0.84 mmol), and tetramethylammonium hydroxide pentahydrate (15 mg, 0.08 mmol) followed by 2-bromoethanol (39 μL, 0.46 mmol). The mixture was stirred at 50° C. under N$_{2(g)}$ and aliquots of 2-bromoethanol (3×20 μL) were added at 24 hour intervals. Extractive workup and chromatography analogous to that described in Example 1 followed by conversion to the HCl salt as outlined for Example 2 afforded 76 mg (53%) of product. (M.P. 215°–217° C.; LC-MS: 342 (MH$^+$); anal. RP18-HPLC RT: 4.09 min.).

Example 68

3-[4-(6-Chloro-2,3-dihydro-indol-1-yl)-quinazolin-7-yloxy]-propan-1-ol hydrochloride salt To 4-(6-chloro-2,3-dihydro-indol-1-yl)-quinazolin-7-ol (125 mg, 0.42 mmol; from Example 65) in DMF (2 mL) was added H$_2$O (50 μL), K$_2$CO$_3$(s) (116 mg, 0.84 mmol) and tetramethylammonium hydroxide pentahydrate (15 mg, 0.08 mmol) followed by 3-bromopropanol (43 μL, 0.46 mmol). The mixture was stirred at 50° C. under N$_{2(g)}$ for 24 hours before another aliquot (11 μL) of 3-bromopropanol was added. After heating another 24 hours, extractive workup and chromatography analogous to that described in Example 1 followed by conversion to the HCl salt as outlined for Example 2 afforded 119 mg (70%) of product. (M.P. 211°–223° C. (dec); LC-MS: 356 (MH$^+$); anal. RP18-HPLC RT: 4.40 min.; M.P. of free-base: 137°–138° C.).

Examples 69 & 70

4-6-Chloro-2,3-dihydro-indol-1-yl)-quinazoline-6,7-diol and 4-6-Chloro-2,3-dihydro-indol-1-yl)-6-methoxy-quinazolin-7-ol 4-(5-Chloro-2,3-dihydro-indol-1-yl)-6,7-dimethoxy-quinazoline (1.00 g, 2.93 mmol; from Example 3) was added to molten pyridinium hydrochloride (10.14 g, 88 mmol) at 170° C. The mixture was stirred at 170° C. for 0.5–1.0 hours (until <5% starting material remained by anal. RP-HPLC), and then poured into ice/water (110 mL). The precipitated orange solid was recovered by filtration, dried by azeotropic removal of H$_2$O with CH$_3$CN at 40° C. in vacuo, dissolved in 15% i-PrOH/CHCl$_3$ (75 mL) and washed with saturated aqueous NaHCO$_3$ (2×). The organic phase was dried over Na$_2$SO$_{4(s)}$, filtered and concentrated in vacuo. The residue (~800 mg) was triturated with CHCl$_3$ (60 mL) and filtered to recover the 6,7-diol (typically 200 mg, 94% purity; used without further purification)(M.P. 200° C. (dec); LC-MS: 314 (MH$^+$); anal. RP18-HPLC RT: 4.07 min.). The filtrate was flash chromatographed on silica (40 to 80% acetone/CH$_2$Cl$_2$) to afford ~550 mg of the pure 6-methoxy-quinazolin-7-ol product (M.P. 175° C. (dec); LC-MS: 328 (MH$^+$); anal. RP18-HPLC RT: 4.07 min.).

Example 71

4-(6-Chloro-2,3-dihydro-indol-1-yl)-6-methoxy-7-(2-methoxy-ethoxy)-quinazoline methanesulfonate salt 4-(6-Chloro-2,3-dihydro-indol-1-yl)-6-methoxy-quinazolin-7-ol (100 mg, 0.305 mmol; from Example 70) was reacted with 2-bromoethyl methyl ether as described in Example 66 and worked-up as described for Example 1 to yield 53 mg of product which was converted to the methanesulfonate salt as outlined in Example 44. (M.P. 248° C. (dec); LC-MS: 386 (MH$^+$); anal. RP18-HPLC RT: 4.56 min.).

Example 72

4-(6-Chloro-2,3-dihydro-indol-1-yl)-6,7-bis-(2-methoxy-ethoxy)-quinazoline methanesulfonate salt To 4-(6-Chloro-2,3-dihydro-indol-1-yl)-quinazoline-6,7-diol (250 mg, 0.797 mmol; from Example 69) dissolved in DMF (4 mL) was added H$_2$O (50 μL), K$_2$CO$_3$(s) (330 mg, 2.39 mmol), and tetramethylammonium hydroxide pentahydrate (15 mg, 0.08 mmol) followed by 2-bromoethyl methyl ether (225 μL, 2.39 mmol). The mixture was stirred at 50° C. under N$_{2(g)}$ for 5 hours and then worked-up as described for Example 1 to yield 131 mg of product which was converted to the methanesulfonate salt as outlined in Example 44. (M.P. 185° C. (dec); LC-MS: 430 (MH$^+$); anal. RP18-HPLC RT: 4.68 min.).

Examples 73 & 74

[4-(6-Chloro-2,3-dihydro-indol-1-yl)-6-methoxy-quinazolin-7-yloxy]-acetic acid ethyl ester and [4-(6-Chloro-2,3-dihydro-indol-1-yl)-6-methoxy-quinazolin-7-yloxy]-acetic acid lithium salt To 4-(6-chloro-2,3-dihydro-indol-1-yl)-6-methoxy-quinazolin-7-ol (128 mg, 0.333 mmol; from Example 70) in DMF (2 mL) was added potassium tert-butoxide (0.381 mL of 1.0M in THF) followed within minutes by ethyl 2-bromoacetate (47 μL, 0.420 mmol). The mixture was stirred for 16 hours at 20° C., and then partitioned between CHCl$_3$ and 5% aqueous NaHCO$_3$. The organic phase was washed with brine, dried over Na$_2$SO$_{4(s)}$, filtered and concentrated in vacuo. The residue was recrystallized from CHCl$_3$/hexane to afford 30 mg of the ester as a pale yellow solid. (M.P. 175°–176° C.; GC-MS: 413 (M$^+$); anal. RP18-HPLC RT: 5.34 min.).

The filtrate from the recrystallization was dissolved in MeOH (6mL) and H$_2$O (3 mL) and LiOH (30 mg, 0.666 mmol) was added. The mixture was heated to reflux for 1 hour, and the volume was reduced ~65% in vacuo before washing the aqueous phase with Et$_2$O. The pH of the aqueous phase was adjusted to 3.5 using AcOH and the mixture was chilled to 4° C. to precipitate the free-acid product (73 mg), which was converted to its lithium salt by treatment with 1.00 eq. of LiOH in MeOH and precipitation on dilution with Et$_2$O. (M.P. 240°–255° C. (dec); NEG-FAB: 390 (M—H$^-$); anal. RP18-HPLC RT: 3.00 min.).

Example 75

2-[4-(6-Chloro-2,3-dihydro-indol-1-yl)-6-methoxy-quinazolin-7-yloxy]-ethanol methanesulfonate salt To 4-(6-chloro-2,3-dihydro-indol-1-yl)-6-methoxy-quinazolin-7-ol (271 mg, 0.828 mmol; from Example 70) in DMF (3 mL) was added tetramethylammonium hydroxide pentahydrate (75 mg, 0.305 mmol), K$_2$CO$_{3(s)}$ (171 mg, 1.24 mmol) and H$_2$O (50 µL) followed by 2-bromoethanol (79 µL, 1.11 mmol). The mixture was stirred at 50° C. and further additions of 2-bromoethanol (1.0 eq.) were made daily. After 4 days the mixture was partitioned between CHCl$_3$ and brine. The organic phase was washed with saturated aqueous NaHCO$_3$ and brine, dried over Na$_2$SO$_{4(s)}$, filtered and concentrated in vacuo. Flash chromatography (40% acetone/CH$_2$Cl$_2$) of the residue on silica yielded 269 mg (87%) of the free-base (M.P. 205°–206° C.) which was converted to a hydrochloride salt according to the analogous method in Example 2 (M.P. 190°–204° C. (dec).), or a methanesulfonate salt by the analogous method in Example 44. (M.P. 233°–237° C. (dec); LC-MS: 372 (MH$^+$); anal. RP18-HPLC RT: 3.90 min.).

Example 76

4-(6-Chloro-2,3-dihydro-indol-1-yl)-6-methoxy-7-(2-morpholin-4-yl-ethoxy)-quinazoline bis (methanesulfonate) salt To a stirred solution of 4-(6-chloro-2,3-dihydro-indol-1-yl)-6-methoxy-quinazolin-7-ol (200 mg, 0.610 mmol; from Example 70) and triphenylphosphine(160 mg, 0.610 mmol) in dry THF (3 mL) under N$_{2(g)}$ was added diethyl-azodicarboxylate (106 µL, 0.671 mmol) dropwise at 0° C. over 10 minutes followed by a solution of 4-(2-hydroxyethyl)-morpholine (81 µL, 0.671 mmol) in dry THF (0.8 mL). The mixture was allowed to warm to 20° C. and stirred 16 hours before quenching with H$_2$O (20µL) and concentrating in vacuo. Flash chromatography of the residue on silica using first 45% acetone/CH$_2$Cl$_2$ followed by 10% MeOH/CH$_2$Cl$_2$ eluted the product as its free-base (180 mg), which was precipitated as its bis(methanesulfonate) salt by addition of 2.0 eq. of methanesulfonic acid to a solution in CH$_2$Cl$_2$. (M.P. 150°–158° C. (dec); LC-MS: 441 (MH$^+$); anal. RP18-HPLC RT: 3.76 min.).

Example 77

4-(6-Chloro-2,3-dihydro-indol-1-yl)-7-(2-imidazol-1-yl-ethoxy)-6-methoxy-quinazoline bis (methanesulfonate) salt This product was produced in 50% yield from 4-(6-chloro-2,3-dihydro-indol-1-yl)-6-methoxy-quinazolin-7-ol and N-(2-hydroxyethyl)imidazole (1.1 eq.) in a manner analogous to that described for Example 76. (M.P. 162°–168° C. (dec); LC-MS: 422 (MH$^+$); anal. RP18-HPLC RT: 3.94 min.).

Example 78

1-[4-(6-Chloro-2,3-dihydro-indol-1-yl)-6-methoxy-quinazolin-7-yloxy]-3-methoxy-propan-2-ol methanesulfonate salt To 4-(6-chloro-2,3-dihydro-indol-1-yl)-6-methoxy-quinazolin-7-ol (125 mg, 0.381 mmol; from Example 70) in DMF (2 mL) was added tetramethylammonium hydroxide pentahydrate (15 mg, 0.076 mmol), K$_2$CO$_{3(s)}$ (79 mg, 0.572 mmol) and H$_2$O (50 µL) followed by methyl glycidyl ether (37 µL, 0.42 mmol). The mixture was stirred at 50° C. and further additions of methyl glycidyl ether (0.5 eq.) were made daily. After 4 days the mixture was partitioned between CHCl$_3$ and brine. The organic phase was washed with saturated aqueous NaHCO$_3$ and brine, dried over Na$_2$SO$_{4(s)}$, filtered and concentrated in vacuo. Flash chromatography (25->40% acetone/CH$_2$Cl$_2$) of the residue on silica yielded 56% of the free-base (M.P. 89°–90° C.) which was converted to the methanesulfonate salt as outlined in Example 44. (M.P. 180°–187° C. (dec); LC-MS: 416 (MH$^+$); anal. RP18-HPLC RT: 3.81 min.).

Example 79

2-[4-(6-Chloro-2,3-dihydro-indol-1-yl)-6-methoxy-quinazolin-7-yloxy]-propanol methanesulfonate salt To 4-(6-chloro-2,3-dihydro-indol-1-yl)-6-methoxy-quinazolin-7-ol (328 mg, 1.0 mmol; from Example 70) in DMF (2 mL) was added tetramethylammonium hydroxide pentahydrate (27 mg, 0.2 mmol), K$_2$CO$_{3(s)}$ (276 mg, 2.0 mmol) and H$_2$O (50 µL) followed by 3-bromopropanol (90 µL, 1.0 mmol). The mixture was stirred at 50° C. for 16 hours. Following extractive work-up, chromatography on silica (55% acetone/hexanes)(M.P. of free-base: 152°–153° C.), and salt formation analogous to that described for Example 78 the product was obtained in 84% yield. (M.P. 195°–205° C. (dec); LC-MS: 386 (MH$^+$); anal. RP18-HPLC RT: 3.95 min.).

Example 80

[4-(6-Chloro-2,3-dihydro-indol-1-yl)-7,8-dihydro-[1,4]dioxino[2,3-g]quinazolin-7-yl]-methanol To 4-(6-Chloro-2,3-dihydro-indol-1-yl)-quinazoline-6,7-diol (99 mg, 0.316 mmol; from Example 69) dissolved in DMF (2 mL) was added H$_2$O (100 µL), K$_2$CO$_3$(s) (65 mg, 0.473 mmol), and tetramethylammonium hydroxide pentahydrate (11 mg, 0.06 mmol) followed by epibromohydrin (28 µL, 0.331 mmol). The mixture was stirred at 50° C. under N$_{2(g)}$ for 16 hours. Following extractive work-up, and chromatography on silica (20% acetone/CH$_2$Cl$_2$) analogous to that described for Example 78 the product was obtained in 11% yield. (M.P. 219°–222° C. (dec); LC-MS: 370 (MH$^+$); anal. RP18-HPLC RT: 3.98 min.).

Example 81

4-(6-Bromo-6-fluoro-2,3-dihydro-indol-1-yl)-6,7-bis-(2-methoxy-ethoxy)-quinazoline hydrochloride salt Utilizing a procedure analogous to that described in Example 1, this product was prepared in 78% yield from 6-bromo-5-fluoro-indoline (1.1 eq.), and 4-chloro-6,7-bis- (2-methoxy-ethoxy)-quinazoline (1.0 eq) in i-PrOH. (M.P. of free-base: 146°–148° C.)(For HCl salt: M.P. 215°–223° C. (dec); LC-MS: 492, 494 (MH$^+$); anal. RP18-HPLC RT: 4.64 min.).

Example 82

4-(6-Bromo-6-fluoro-2,3-dihydro-indol-1-yl)-6-methoxy-7-(2-methoxy-ethoxy)-quinazoline hydrochloride salt Utilizing a procedure analogous to that described in Example 1, this product was prepared in 58% yield from 6-bromo-5-fluoro-indoline (1.1 eq.), and 4-chloro-6-methoxy-7-(2-methoxy-ethoxy)-quinazoline (1.0 eq) in i-PrOH. (M.P. of free-base: 150°–150.5° C.)(For HCl salt: M.P. 243°–251° C. (dec); LC-MS: 448, 450 (MH$^+$); anal. RP18-HPLC RT: 4.79 min.).

Example 83

1-(6,7-Dimethoxy-quinazolin-4-yl)-2,3-dihydro-1H-indol-5-ylamine hydrochloride salt The (6-nitro-indolin-1-yl)-6,7-dimethoxy-quinazoline (412 mg, 1.17 mmol) produced in Example 52 was hydrogenated under 50 psi of H$_2$(g) in MeOH (10 mL)/HOAc (20 mL) with 11.7 M HCl (2 mL) in the presence of 10% Pd-C (200 mg) for 24 hours. Following workup analogous to that described in Example 30 and chromatography on silica (5% MeOH/CH$_2$Cl$_2$) gave the product (91%, 372 mg) which was converted to the HCl salt analogous to that in Example 2. (M.P. 277°–280° C. (dec); LC-MS: 323 (MH$^+$); anal. RP18-HPLC RT: 2.74 min.).

Example 84

1-(6,7-Dimethoxy-quinazolin-4-yl)-2,3-dihydro-1H-indole-2-carboxylic acid lithium salt To 1-(6,7-dimethoxy-quinazolin-4-yl)-2,3-dihydro-1H-indole-2-carboxylic acid methyl ester (500 mg, 1.37 mmol; from Example 24) in MeOH (8 mL)/H$_2$O (4 mL) was added LiOH (56 mg, 1.37 mmol). The solution was heated briefly to reflux (~5 minutes) and cooled to 20° C. and concentrated in vacuo to afford the lithium salt of the acid. (FAB-MS: 352 (MH$^+$), 358 (M—H+Li)$^+$; anal. RP18-HPLC RT: 2.53 min.).

Example 85

N-[1-(6,7-Dimethoxy-quinazolin-4-yl)-2,3-dihydro-1H-indol-6-yl]-acetamide

To 1-(6,7-dimethoxy-quinazolin-4-yl)-2,3-dihydro-1H-indol-6-ylamine (99 mg, 0.307 mmol; from Example 30) and pyridine (32 µL, 0.620 mmol) in CHCl$_3$ (5 mL) was added acetyl chloride (33 µL, 0.455 mmol). The mixture was refluxed 2 hours, diluted with CHCl$_3$ (15 mL), and the organic solution was washed with saturated aqueous NaHCO$_3$, dried over Na$_2$SO$_{4(s)}$, filtered and concentrated in vacuo. Flash chromatography on silica (5% MeOH/CHCl$_3$) afforded 77 mg of product. (M.P. 223°–229° C. (dec); GC-MS: 364 (M$^+$); anal. RP18-HPLC RT: 3.42 min.).

Example 86

N-[1-(6,7-Dimethoxy-quinazolin-4-yl)-2,3-dihydro-1H-indol-6-yl]-2,2,2-trifluoro-acetamide To 1-(6,7-dimethoxy-quinazolin-4-yl)-2,3-dihydro-1H-indol-6-ylamine (119 mg, 0.369 mmol; from Example 30) and pyridine (42 µL, 0.79 mmol) in CH$_2$Cl$_2$ (5 mL) was added trifluoroacetic anhydride (112 µL, 0.79 mmol). The mixture was stirred at 20° C. for 6 hours, quenched with H$_2$O (5 mL), stirred 30 minutes and diluted with CHCl$_3$ (15 mL). The organic phase was separated and washed with saturated aqueous NaHCO$_3$, dried over Na$_2$SO$_{4(s)}$, filtered and concentrated in vacuo. Flash chromatography on silica (3% MeOH/CHCla) afforded 109 mg of product. (M.P. 240° C. (dec); GC-MS: 418 (M$^+$); anal. RP18-HPLC RT: 4.20 min.).

Example 87

N-[1-(6,7-Dimethoxy-quinazolin-4-yl)-2,3-dihydro-1H-indol-5-yl]-acetamide

To 1-(6,7-dimethoxy-quinazolin-4-yl)-2,3-dihydro-1H-indol-5-ylamine (102 mg, 0.316 mmol; free-base from Example 83) and 4-(N,N-dimethylamino)pyridine (51.2 mg, 0.42 mmol) in CH$_2$Cl$_2$ (5 mL) was added acetic anhydride (88 µL, 0.93 mmol). The mixture was stirred at 20° C. for 7.5 hours, quenched with H=O (5 mL), stirred 30 min. and diluted with CHCl$_3$ (15 mL). The organic phase was separated and washed with saturated aqueous NaHCO$_3$, dried over Na$_2$SO$_{4(s)}$, filtered and concentrated in vacuo. Flash chromatography on silica (3.5% MeOH/CHCl$_3$) afforded 53 mg of product. (M.P. >250° C. (dec); LC-MS: 365 (MH$^+$); anal. RP18-HPLC RT: 2.79 min.).

Example 88

N-[1-(6,7-Dimethoxy-quinazolin-4-yl)-2,3-dihydro-1H-indol-5-yl]-formamide

Formic acid (42 µL) was added to acetic anhydride (88 µL) while stirring at 5° C. and the mixture was allowed to stir at 20° C. for 1 hour before adding 1-(6,7-dimethoxy-quinazolin-4-yl)-2,3-dihydro-1H-indol-5-ylamine (102 mg, 0.316 mmol; freebase from Example 83). The mixture was stirred at 20° C. for 1.5 hours, quenched with H$_2$O (5 mL), stirred 30 min. and diluted with CHCl$_3$ (15 mL). The organic phase was separated and washed with saturated aqueous NaHCO$_3$, dried over Na$_2$SO$_{4(s)}$, filtered and concentrated in vacuo. Flash chromatography on silica (4% MeOH/CH$_2$Cl$_2$) afforded 66 mg of product. (M.P. 239°–244° C. (dec); LC-MS: 351 (MH$^+$); anal. RP18-HPLC RT: 2.92 min.).

Example 89

8-Bromo-1-(6,7-dimethoxy-quinazolin-4-yl)-2,3,4,5-tetrahydro-1H-benzo[b]azepine

Utilizing a procedure analogous to that described in Example 47, this product was prepared in 58% yield from 8-bromo-2,3,4,5-tetrahydro-1H-benzo[b]azepine (1.1 eq.), and 4-chloro-6,7-dimethoxy-quinazoline (1.0 eq) in N-methyl-pyrrolidinone. (M.P. 209°–217° C.; LC-MS: 414, 416 (MH$^+$); anal. RP18-HPLC RT: 5.47 min.).

Example 90

1-(6,7-Dimethoxy-quinazolin-4-yl)-1,2,3,4,5,6-hexahydro-benzo[b]azocine

Utilizing a procedure analogous to that described in Example 47, this product was prepared in 67% yield from 1,2,3,4,5,6-hexahydro-benzo[b]azocine (1.1 eq.), and 4-chloro-6,7-dimethoxy-quinazoline (1.0 eq) in N-methyl-pyrrolidinone. (M.P. 204°–207° C.; GC-MS: 349 (M$^+$); anal. RP18-HPLC RT: 5.25 min.).

Example 91

4-(6-Chloro-2,3-dihydro-indol-1-yl)-6-methoxy-quinazoline

Utilizing a procedure analogous to that described in Example 1, this product was prepared in 77% yield from 6-chloro-indoline and 4-chloro-6-methoxy-quinazoline. (M.P. 243° C.; LC-MS: 312 (MH$^+$)).

Example 92

4-(3,4-Dihydro-2H-quinolin-1-yl)-7-methoxy-6-methylsulfanyl-quinazoline

Utilizing a procedure analogous to that described in Example 1, this product was prepared in 35% yield from 1,2,3,4-tetrahydroquinoline and 4-chloro-7-methoxy-6-methylsulfanyl-quinazoline. (M.P. 193°–196° C.; LC-MS: 338 (MH$^+$)).

Example 93

4-(6-Chloro-2,3-dihydro-indol-1-yl)-6-methyl-quinazoline

Utilizing a procedure analogous to that described in Example 24, this product was prepared in 15% yield from 6-chloro-indoline and 4-chloro-6-methyl-quinazoline. (M.P. 138°–41° C.; LC-MS: 296 (MH$^+$)).

Example 94

4-(6-Chloro-2,3-dihydro-indol-1-yl)-7-methoxy-6-methylsulfanyl-quinazoline

Utilizing a procedure analogous to that described in Example 1, this product was prepared in 18% yield from 6-chloro-indoline and 4-chloro-7-methoxy-6-methylsulfanyl-quinazofine. (M.P. 210° C.; LC-MS: 358 (MH$^+$)).

Example 95

4-(6-Chloro-2,3-dihydro-indol-1-yl)-6,7-dimethyl-quinazoline

Utilizing a procedure analogous to that described in Example 24, this product was prepared in 16% yield from 6-chloro-indoline and 4-chloro-6,7-dimethyl-quinazoline. (M.P. 199° C.; LC-MS: 310 (MH$^+$)).

Example 96

7-Chloro-4-(6-chloro-2,3-dihydro-indol-1-yl)-6-(2-methoxy-ethylsulfanyl)-quinazoline Utilizing a procedure analogous to that described in Example 1, this product was prepared in 38% yield from 6-chloro-indoline and 4,7-dichloro-6-(2-methoxy-ethylsulfanyl)quinazofine. (M.P. 104°–106° C.; LC-MS: 406 (MH$^+$)).

Example 97

7-Chloro-4-(6-chloro-2,3-dihydro-indol-1-yl)-quinazoline

Utilizing a procedure analogous to that described in Example 24, this product was prepared in 50% yield from 6-chloro-indoline and 4,7-dichloro-quinazoline. (M.P. 189° C.; LC-MS: 316 (MH$^+$)).

Example 98

8-Chloro-4-(6-chloro-2,3-dihydro-indol-1-yl)-quinazoline

Utilizing a procedure analogous to that described in Example 24, this product was prepared in 47% yield from 6-chloro-indoline and 4,8-dichloro-quinazoline. (M.P. 190° C.; LC-MS: 316 (MH$^+$)).

Example 99

(6-Chloro-4-(6-chloro-2,3-dihydro-indol-1-yl)-7-methoxy-quinazoline

Utilizing a procedure analogous to that described in Example 1, this product was prepared in 17% yield from 6-chloro-indoline and 4,6-dichloro-7-methoxy-quinazoline. (M.P. 226° C.; LC-MS: 346 (MH$^+$)).

Example 100

(7-Chloro-4-(6-chloro-2,3-dihydro-indol-1-yl)-6-methylsulfanyl-quinazoline

Utilizing a procedure analogous to that described in Example 1, this product was prepared in 15% yield from 6-chloro-indoline and 4,7-dichloro-6-methylsulfanyl-quinazoline. (M.P. 167°–168° C.; LC-MS: 362 (MH$^+$)).

Example 101

(4-(6-Chloro-2,3-dihydro-indol-1-yl)-7-methyl-quinazoline

Utilizing a procedure analogous to that described in Example 24, this product was prepared in 14% yield from 6-chloro-indoline and 4-chloro-7-methyl-quinazoline. (M.P. 265° C.; LC-MS: 296 (MH$^+$)).

Example 102

(4-(5-Bromo-3,4-dihydro-2H-quinolin-1-yl)-6,7-dimethoxy-quinazoline

Utilizing a procedure analogous to that described in Example 1, this product was prepared in 4% yield from 5-bromo-1,2,3,4-tetrahydroquinoline and 4-chloro-6,7-dimethoxy-quinazoline. (film; LC-MS: 399 (MH$^+$)).

Example 103

4-(7-Bromo-3,4-dihydro-2H-quinolin-1-yl)-6,7-dimethoxy-quinazoline

Utilizing a procedure analogous to that described in Example 1, this product was prepared in 11% yield from 7-bromo-1,2,3,4-tetrahydroquinoline and 4-chloro-6,7-dimethoxy-quinazoline. (film; LC-MS: 399 (MH$^+$)).

Example 104

[(4-(3,4-Dihydro-2H-quinolin-1-yl)-6-methoxy-quinazolin-7-yloxyl-acetic acid ethyl ester Utilizing a procedure analogous to that described in Example 1, this product was prepared in 2% yield from 1,2,3,4-tetrahydroquinoline and (4-chloro-6-methoxy-quinazolin-7-yloxy)-acetic acid ethyl ester. (film; LC-MS: 393 (MH$^+$)).

Example 105

[(4-(3,4-Dihydro-2H-quinolin-1-yl)-7-ethoxycarbonylmethoxy-quinazolin-6-yloxyl-acetic acid ethyl ester Utilizing a procedure analogous to that described in Example 1, this product was prepared in 19% yield from 1,2,3,4-tetrahydroquinoline and (4-chloro-7-ethoxycarbonylmethoxy-quinazolin-6-yloxy)-acetic acid ethyl ester. (film; LC-MS: 465 (MH$^+$)).

Example 106

4-(6-Chloro-2,3-dihydro-indol-1-yl)-7-nitro-quinazoline hydrochloride

4-Chloro-7-nitroquinazoline (11.22 g, 53.5 mmol) was slurried into 35 ml isopropanol, treated with 6-chloroindoline (8.25 g, 53.7 mmol), refluxed for three hours, then cooled slowly to room temperature. Product was filtered and air dried overnight to afford bright yellow powder; 13.18 g (68%): M.P. 230° C. (dec); LC-MS: 327 (MH$^+$), 329 ((M+2)H$^+$); Calc. $C_{16}H_{11}ClN_4O_2 \cdot HCl$: C,52.91; H,3.3; N,15.43; Cl,19.52; Found: C,52.77; H,3.61; N,14.78; Cl,19.62.

Example 107

4-(6-Chloro-2,3-dihydro-indol-1-yl)-quinazolin-7-yl amine hydrochloride 4-(6-Chloro-2,3-dihydro-indol-1-yl)-7-nitro-quinazoline hydrochloride (2.16 g, 5.90 mmol) was slurried in 250 mL of ethanol containing 0.21 g of 10% paladium on carbon and treated with ammonium formate (1.68 g, 26.6 mmol). After 16 hours the mixture was filtered through celite and evaporated in vacuo to a residue. This was dissolved in chloroform, filtered and washed with sodium bicarbonate and brine then dried with magnesium sulfate, filtered and evaporated in vacuo to give crude product which was recrystallized from 50% aqueous ethanol. The solid was dissolved in methanol containing anhydrous hydrogen chloride and poured into ether to yield the title compound after filtration and drying in vacuo; 0.687 g (35%) M.P. 282°–283° C.

Example 108

N-[4-(6-Chloro-2,3-dihydro-indol-1-yl)-quinazolin-7-yl]methanesulfonamide 4-(6-Chloro-2,3-dihydro-indol-1-yl)-quinazolin-7-yl amine hydrochloride (0.155 g, 0.465 mmol) was reacted with methanesulfonyl chloride (0.0531, 0.465 mmol) and triethylamine (0.290 g, 2.87 mmol) in 5 mL of chloroform at 0° C. for one hour and 16 hours at room temperature. The reaction mixture was poured into 50 mL of water and extracted with 3×50 mL of ethyl acetate. The pooled organic layers were washed with 50 mL of brine, dried with magnesium sulfate, filtered and vacuum evaporated to a yellow residue, 0.121 g. This was purified by chromatography using a Chromatotron mounted with a 2 mm silica gel plate and eluted with 5% methanol in chloroform. Pure product was isolated by vacuum evaporation of the appropriate fractions; 0.015 g (8.7%) M.P. 240°–245° C. (dec).

Example 109

N-[4-(6-Chloro-2,3-dihydro-indol-1-yl)-quinazolin-7-yl]bismethanesulfonamide 4-(6-Chloro-2,3-dihydro-indol-1-yl)-quinazolin-6-yl-amine hydrochloride (0.1495 g, 0.449 mmol) was slurried into 5 mL methylene chloride. Triethylamine (1.2 mL, 8.6 mmol) was added and the reaction was cooled to 0° C. Methanesulfonyl chloride (0.105 mL, 1.36 mmol) was added and the reaction warmed to room temperature. After 30 minutes, the mixture was poured into 20 mL water, extracted with methylene chloride (3×20 mL), washed with saturated aqueous sodium bicarbonate and with brine, dried over magnesium sulfate, filtered, and solvent removed in vacuo to afford yellow foam, 0.177 g (87%); LC-MS: 453 (MH$^+$), 455 ((M+2)H$^+$).

Example 110

N-[4-(6-Chloro-2,3-dihydro-indol-1-yl)-quinazolin-7-yl]-hydroxylamine 4-(6-Chloro-2,3-dihydro-indol-1-yl)-7-nitro-quinazoline hydrochloride (2.90 g, 7.98 mmol) was dissolved in 700 mL methanol and hydrogenated with 10% palladium on carbon (0.50 g) for 10 minutes at 3 atm. Reaction mixture was filtered through celite and diluted with 1.5 L diethyl ether. Product was filtered and dried under vacuum to give bright yellow solid, 2.23 g (80%):M.P. 262°–263° C. (dec); GC-MS: 313 (M$^+$), 315 (M$^+$+2); Calc. $C_{16}H_{13}ClN_4O \cdot HCl$: C,55.03; H,4.04; N,16.04; Found: C,55.18; H,4.28; N,16.13.

Example 111

[4-(6-Chloro-2,3-dihydro-indol-1-yl)-quinazolin-7-yl]-methylamine hydrochloride 4-(6-Chloro-2,3-dihydro-indol-1-yl)-quinazolin-7-ylamine hydrochloride (0.104 g, 0.313 mmol) was dissolved in 3 mL acetonitrile and treated with 0.141 mL 37% aqueous formaldehyde (1.74 mmol). Sodium cyanoborohydride (0.036 g, 0.571 mmol) was added slowly, then 0.05 mL acetic acid was added and the reaction was stirred at room temperature for two hours. Additional formaldehyde (1.74 mmol) and sodium cyanoborohydride (0.571 mmol) were added after thirty minutes, additional acetic acid (0.05 mL) was added at thirty minutes and at one hour. After two hours, the reaction mixture was poured into 50 mL diethyl ether and washed with 1N sodium hydroxide (3×50 mL), dried over magnesium sulfate, filtered and solvent removed in vacuo to give 0.913 yellow solid containing cyanohydroboramine derivatives of both monomethylated and dimethylated material.

Automated rotary thin-layer chromatography (Chromatotron®) using a 2 mm silica gel plate and eluting with chloroform, then 10% methanol in chloroform gave 0.0156 g of the cyanohydroboramine derivative of the monomethylated material, which was dissolved in 1 mL ethanol and treated with 0.8 mL 1N HCl in methanol and refluxed overnight. The resulting mixture was poured into 100 mL 1N sodium hydroxide, extracted with chloroform (4×50 mL), dried over magnesium sulfate, filtered and solvent removed in vacuo. Resulting yellow residue was dissolved in minimal methanol, treated with 1N HCl in methanol, precipitated by dilution with diethyl ether, filtered and dried in vacuo to give bright yellow solid, 0.010 g (9%): M.P. 270°–274° C. (dec); LC-MS: 311 (MH$^+$), 313 ((M+2)H$^+$).

Example 112

[4-(6-Chloro-2,3-dihydro-indol-1-yl)-quinazolin-7-yl]-dimethylamine hydrochloride Cyanohydroboramine derivative of the dimethylated material isolated by Chromatotron chromatography in Example 111 was treated in an identical manner with ethanolic HCl to give bright yellow solid, 0.0145 g (13%): M.P. 281°–282° C. (dec); LC-MS: 325 (MH$^+$), 327 ((M+2)H$^+$).

Example 113

4-(6-Chloro-2,3-dihydro-indol-1-yl)-6-nitro-quinazoline

4-Chloro-6-nitroquinazoline (16.72 g, 79.8 mmol) was slurried into 250 ml isopropanol, treated with 6-chioroindoline (12.25 g, 79.8 mmol), refluxed for three hours, then cooled slowly to room temperature. Product was filtered and air dried overnight to afford 12.30 g of a bright yellow powder. This was heated at reflux in 100 mL of chloroform containing 15 mL of triethylamine for one hour. The cool suspension was filtered to afford pure title compound; 5.17 g (20%); M.P. 260°–261° C. (dec).

Example 114

N-[4-(6-Chloro-2,3-dihydro-indol-1-yl)-quinazolin-6-yl]-formamide 4-(6-Chloro-2,3-dihydro-indol-1-yl)-7-nitro-quinazoline (5.17 g, 15.8 mmol) was dissolved in 60 mL 96% formic acid. Sodium dithionite (13.78 g, 79.2 mmol) was added slowly, ice bath was used to control reaction temperature. After 30 minutes, about half of the formic acid was removed in vacuo,, and the remaining reaction mixture was poured into water and chloroform and basified to pH 13 with 6N NaOH, extracted with chloroform (3×100 mL), washed with brine (100 mL), added over magnesium sulfate, filtered and solvent removed in vacuo to give bright yellow foam, 2.71 g (53%): LC-MS: 325 (MH$^+$), 327 ((M+2)H$^+$).

Example 115

4-(6-Chloro-2,3-dihydro-indol-1-yl)-quinazolin-6-ylamine hydrochloride

N-[4-(6-Chloro-2,3-dihydro-indol-1-yl)-quinazolin-6-yl]-formamide (1.0055 g, 3.10 mmol) was slurried into 20 mL methanol, treated with 20 mL 1N HCl in methanol, and stirred at room temperature for one hour. Dilution to 125 mL with diethyl ether afforded yellow solid, 0.8430 g (82%; another 0.089 g obtained from subsequent cooling of mother liquor): M.P. 289°–290° C. (dec); LC-MS: 297 (MH$^+$), 299 ((M+2)H$^+$).

Example 116

4-(6-Chloro-2,3-dihydro-indol-1-yl)-quinazolin-6-yl]-methylamine

N-[4-(6-Chloro-2,3-dihydro-indol-1-yl)-quinazolin-6-yl]-formamide (0.5010 g, 1.54 mmol) in 6 mL tetrahydrofuran was added to a slurry of lithium aluminum hydride (0.1726 g, 4.55 mmol) in 5 mL tetrahydrofuran dropwise over 10 minutes. The reaction was stirred at room temperature for 15 minutes, then quenched by successive addition of 0.2 mL water, 0.2 mL 1N sodium hydroxide (aq) and 0.6 mL water, then was filtered and the filter cake washed thoroughly with water and ethyl acetate. The filtrate was extracted with ethyl acetate (3×50 mL), washed with brine (100 mL), dried over magnesium sulfate, filtered and solvent removed in vacuo. The residue was slurried into 10 mL methanol, treated with 10 mL 1N HCl in methanol, and precipitated with 200 mL diethyl ether. The precipitate was collected and dried under vacuum to afford bright yellow solid, 0.312 g (64%): M.P. 259°–261° C. (dec); LC-MS: 311 (MH$^+$), 313 ((M+2)H$^+$); Calc $C_{17}H_{15}ClN_4 \cdot HCl \cdot 1.5H_2O$: C,54.55; H,5.12; N,14.97; Found: C,54.27; H,5.00; N,14.99

Example 117

N-4-(6-Chloro-2,3-dihydro-indol-1-yl)-quinazolin-6-yl]-N-methyl formamide

The compound of the preceding Example 116 (0.22 g 0.634 mmol) was reacted in 1 mL of a 50% solution of acetic formic anhydride in acetic acid for one hour and precipitated with 10 mL of ethyl ether. The solid thus obtained was filtered and dried in vacuo to give a yellow solid; 0.14 g (67%) M.P. 178°–179° C.

Example 118

N-[4-(6-Chloro-2,3-dihydro-indol-1-yl)-quinazolin-6-yl]-quanidine hydrochloride 4-(6-Chloro-2,3-dihydro-indol-1-yl)-quinazolin-6-ylamine hydrochloride (0.0994 g, 0.298 mmol) was slurried into 3 mL 1,2-dichloroethane and treated with triethylamine (0.0415 mL, 0.298 mmol). Acetic acid (0.250 mL, 4.30 mmol) and 3,5-dimethylpyrazole-1-carboxamide (0.0880 g, 0.632 mmol) were added and the mixture refluxed for 18 hours. After cooling to room temperature, precipitate was collected to afford tan solid, 0.0387 g (35%): M.P. 259°–261° C.; EI-MS: (high resolution) calc. 338.1047; found 338.1042

Example 119

N-[4-(6-Chloro-2,3-dihydro-indol-1-yl)-quinazolin-6-yl]-N',N'-dimethyl-propane-1,3-diamine 4-(6-Chloro-2,3-dihydro-indol-1-yl)-quinazolin-6-ylamine hydrochloride (0.525 g, 1.58 mmol) was combined with 2 mL of freshly distilled 3-dimethylaminopropyl chloride and heated to 120° C. for 1 hour. Yellow liquid was poured off and the remaining red glass was dissolved in water, basified to pH 11 with potassium carbonate, extracted with chloroform (2×50 mL), washed with brine, dried over magnesium sulfate, filtered and stripped to give 0.272 g yellow foam containing starting material and mono- and di-alkylated products. This foam was filtered through silica gel using chloroform, then the product was washed through the silica gel with 40% v/v methanol in chloroform and concentrated in vacuo. The residue was dissolved in methanol, treated with 1N HCl in methanol diluted with diethyl ether, filtered and dried under vacuum to afford a bright yellow solid, 0.0995 g (15%): M.P. 230° C. (dec):LC-MS: 382 (MH$^+$), 384 ((M+2)H$^+$).

Example 120

4-(6-Chloro-2,3-dihydro-indol-1-yl)-6-morpholin-4-yl-quinazoline

4-Chloro-6-morpholino-quinazoline (382 mg, 1.53 mmol) and 6-chloroindoline (258 mg, 1.63 mmol) were heated at reflux in 8 mL of 1,2-dichloroethane and pyridine (264 mg, 3.36 mmol) for 16 hours. The reaction mixture was vacuum evaporated and partitioned between 100 mL of ethyl acetate and 50 mL of 5% sodium bicarbonate. The organic layer was washed with an additional 50 mL of bicarbonate and 50 mL of brine, dried with magnesium sulfate, filtered and evaporated in vacuo to a residue. This was purified by flash chromatography on silica gel eluted with 20% acetone/methylene chloride. The pure solid isolated from the column was converted to its hydrochloride salt by dissolution in methanol containing 1.1 equivalents of anhydrous hydrogen chloride and precipitation with ether; 396 mg (65%); M.P. 277°–279° C.

Example 121

4-(6-Chloro-2,3-dihydro-indol-1-yl)-6-(4-methyl-piperazin-1-yl)-quinazoline 4-Chloro-6-(4-methylpiperazin-1-yl)-quinazoline hydrochloride (537 mg, 1.80 mmol) and 6-chloroindoline (169 mg, 1.10 mmol) were refluxed in 10 mL of 1,2-dichloroethane and pyridine (350 mg, 4.40 mmol) for 48 hours. The product was isolated as the (58%); using the analogous method of Example 120; 267 mg (58%); M.P. 289°–290° C.

Example 122

4-(6-Fluoro-7-methyl-2,3-dihydro-indol-1-yl)-6,7-dimethoxy-quinazoline hydrochloride salt Utilizing a procedure analogous to that described in Example 47 (with conversion to the HCl salt analogous to Example 2), this product was prepared in 58% yield from 6-fluoro-7-methyl-indoline (1.1 eq.), and 4-chloro-6,7-dimethoxy-quinazoline (1.0 eq) in N-methyl-pyrrolidinone. (M.P. 220°–225° C.; LC-MS: 340 (MH$^+$); anal. RP18-HPLC RT: 4.63 min.).

Example 123

1-(6,7-Dimethoxy-quinazolin-4-yl)-2,3,6,7,8,9-hexahydro-1H-benzo[q]indole hydrochloride salt Utilizing a procedure analogous to that described in Example 47 (with conversion to the HCl salt analogous to Example 2), this product was prepared in 58% yield from 2,3,6,7,8,9-hexahydro-1H-benzo[g]indole (1.1 eq.), and 4-chloro-6,7-dimethoxy-quinazoline (1.0 eq) in N-methyl-pyrrolidinone. (M.P. 182°–185° C.; LC-MS: 382 (MH$^+$); anal. RP18-HPLC RT: 5.26 min.).

Example 124

6,7-Dimethoxy-4-(6-trimethylsilanylethynyl-2,3-dihydro-indol-1-yl)-quinazoline

Utilizing a procedure analogous to that described in Example 47, this product was prepared in 93% yield from 6-trimethylsilanylethynyl-indoline (1.1 eq.), and 4-chloro-6,7-dimethoxy-quinazoline (1.0 eq) in N-methyl-pyrrolidinone. (LC-MS: 404 (MH$^+$); anal. RP18-HPLC RT: 6.49 min.).

Example 125

4-(6-Ethynyl-2,3-dihydro-indol-1-yl)-6,7-dimethoxy-quinazoline

To 6,7-dimethoxy-4-(6-trimethylsilanylethynyl-2,3-dihydro-indol-1-yl)-quinazoline (1 eq.; 50 mg; 0.124 mmol) in MeOH (2 mL)/THF (2 mL) was treated with 1M tetrabutylammonium fluoride (2 eq.; 0.248 mL) in THF at 20° C. for 16 hours. Solvents were removed in vacuo and the residue was dissolved in 1:1 EtOAc/Et$_2$O washed with saturated aqueous NaHCO$_3$, dried over Na$_2$SO$_{4(s)}$, filtered and concentrated in vacuo. The product was converted to the HCl salt using a procedure analogous to that described for Example 2. (M.P. 241°–243° C.; LC-MS: 332 (MH$^+$); RP18-HPLC RT: 4.48 min)

Example 126

4-6-Chloro-indol-1-yl)-7-difluoromethoxy-quinazoline

To 4-(6-chloro-2,3-dihydro-indol-1-yl)-quinazolin-7-ol (250 mg, 0.84 mmol; from Example 65) in DMF (BmL) was added KF (49 mg, 0.84 mmol) and K$_2$CO$_3$ (120 mg). Chlorodifluoromethane (Freon22®) was bubbled into the stirred mixture at 0°–5° C. for 5–10 minutes in a pressure tube. The tube was sealed and heated with stirring to 80° C. for 4 hours after which time anal. RP-HPLC detected no remaining starting material. Extractive work-up and flash chromatography on silica (30% acetone/hexanes) as outlined for Example 78 afforded 151 mg (52%) of the difluoromethoxy product which was converted to its hydrochloride salt as outlined in Example 2. (M.P. 250°–256° C. (dec); LC-MS: 348 (MH+); RP18-HPLC RT: 5.64 min)

Example 127

1-(6,7-Dimethoxy-quinazolin-4-yl)-1,2,3,5-tetrahydro-pyrrolo[2,3-f]indole

Utilizing a procedure analogous to that described in Example 24 (with conversion to its HCl salt using a procedure analogous to that described in Example 2), this product was prepared in 67% yield from 1,2,3,5-tetrahydro-pyrrolo[2,3-f]indole (1.1 eq.), and 4-chloro-6,7-dimethoxy-quinazoline (1.0 eq) in DMF. (M.P. 245°–252° C.; LC-MS: 347 (MH+); RP18-HPLC RT: 3.67 min)

Example 128

1-(6,7-Dimethoxy-quinazolin-4-yl)-1,2,3,5,6,7-hexahydro-pyrrolo[2,3-f]indole

Utilizing a procedure analogous to that described in Example 24, this product was prepared in 65% yield from 1,2,3,5,6,7-hexahydro-pyrrolo[2,3-f]indole (1.7 eq.), and 4-chloro-6,7-dimethoxy-quinazoline (1.0 eq) in DMF. (LC-MS: 349 (MH+); RP18-HPLC RT: 3.51 min)

Example 129

{3-[1-(6,7-Dimethoxy-quinazolin-4-yl)-2,3-dihydro-1H-indol-3-yl]-propyl}-dimethyl-amine Utilizing a procedure analogous to that described in Example 24 (with conversion to its HCl salt using a procedure analogous to that as described in Example 2), this product was prepared in 52% yield from 3-(N,N-dimethylamino-propyl)indoline (1.1 eq.), and 4-chloro-6,7-dimethoxy-quinazoline (1.0 eq) in DMF. (M.P. 230°–232° C.; LC-MS: 393 (MH$^+$); anal. RP18-HPLC RT: 3.23 min.).

Preparations

Indolines from Indoles
ZnBH$_4$ Mediated Reduction of Indoles to Indolines

Preparation 1

6-Methyl-indoline

6-Methylindole (2.785 g, 21.2 mmol) in dry Et$_2$O (30 mL) was chilled to 0° C. and a solution of ZnBH$_4$ in Et$_2$O (~1.5 eq.; 215 mL of 0.15M) was added. The mixture was stirred 3 days at 22° C. in darkness and then quenched by addition of 1M aqueous HCl (until no further H$_{2(g)}$ evolved on mixing) followed by basification to pH >10 with 2N NaOH. The ether phase was separated and washed with brine, tided over MgSO$_{4(s)}$, filtered, and concentrated in vacuo to afford >90% pure 6-methyl-indoline as a syrup (2.82 g; GC/MS: RT=0.63 min., M$^+$=133). This material can be purified by chromatography on silica (25% EtOAc/hexanes) or vacuum distillation but was typically used without further purification. The following indolines were prepared in an analogous manner from the appropriately substituted indoles:

| Prep. # | Indoline Product | Yield | GC/MS RT (min) | GC/MS M+ |
|---|---|---|---|---|
| 2 | 4-Methyl | 82% | 0.54 | 133 |
| 3 | 5-Fluoro | 82% | 0.54 | 137 |
| 4 | 6-Bromo* | 90% | 1.12 | 197, 199 |
| 5 | 6-Benzyloxy | 83% | 3.88 | 225 |
| 6 | 6-Methoxy | 81% | 0.94 | 149 |
| 7 | 5-Chloro | 72% | 0.86 | 153 |
| 8 | 5-Methyl | 69% | 0.62 | 133 |
| 10 | 7-Methyl | 89% | 0.59 | 133 |
| 11 | 5,6-Methylene-dioxy | 76% | 1.18 | 163 |
| 12 | 4-Chloro | 85% | 0.806 | 153 |

*6-Bromoindole was prepared by the Batcho-Leimgruber process exactly as described by Moyer, M. P. et al. J. Org. Chem. 51, 5106–5110 (1986).

Borane/Pyridine Mediated Reduction of Indoles

Preparation 13

5-Methoxy-indoline

To 5-methoxy-indole (4.55 g, 31 mmol) suspended in THF (10 mL) at 0°–5° C. was added borane/pyridine complex (15.5 ml of 8M in $BH_3$) followed by dropwise aqueous 6N HCl (50 mL) over 15 min. During the addition THF was added dropwise as required to control foaming. The mixture was stirred 45 min at 20° C., the pH was raised to ~10 by the addition of aqueous NaOH and $Na_2CO_3$, and the mixture was extracted with $CHCl_3$. The organic extracts were washed with brine at pH 9–10 dried over $MgSO_{4(s)}$, filtered, and concentrated in vacuo to afford 5-methoxy-indoline (96%; GC-MS: RT=min, M+=149) which was >97% purity by $^1H$ NMR. This material could be used without further purification, or precipitated pure as its hydrochloride salt by the addition of 1 eq. of 1N HCl in $Et_2O$ to a solution of the free base in EtOAc or ether.

The following indolines were prepared in an analogous manner by treatment of the appropriately substituted indoles with 4–6 eq. of borane/pyridine complex (with 5-hydroxy-indole starting materials generated according to the procedure described below when necessary).

| Preparation # | Indoline Product | Yield | GC/MS RT (min) | GC/MS M+ |
|---|---|---|---|---|
| 14 | 5,7-dichloro | 22% | — | 189* |
| 15 | 6,7-dimethyl | 59% | 0.82 | 147 |
| 16 | 6-fluoro-7-methyl | 56% | 0.93 | 151 |
| 17 | 6,7,8,9-tetrahydro-1H-benzo[g] | 90% | 1.56 | 173 |
| 18 | 6-chloro-5-nitro | 56% | — | 199* |
| 19 | 5-hydroxy | 91% | 1.05 | 135 |
| 20 | 5-hydroxy-6-methyl | 74% | 2.94 | 149 |
| 21 | 5-hydroxy-7-methyl | 57% | 2.83 | 149 |
| 22 | 6-chloro-5-hydroxy | 81% | 2.89 | 169 |
| 23 | 5-hydroxy-6,7-dimethyl | 55% | 1.67 | 163 |
| 24 | 3-(N,N-dimethylamino)propyl | 91% | — | 205* |

*MH+ as observed by LC-MS.

Preparations of Indoles from Anilines

Preparation 25

6,7-Dimethylindole

To a solution of boron trichloride (200 mL of 1M in xylene; 200 mmol) at 0°–5° C. was added 2,3-dimethylaniline (22.2 mL, 182 mmol) in dry toluene (110 mL) dropwise over 20 minutes, followed by 2-chloroacetonitrile (13.8 mL, 218 mmol) dropwise over 10 minutes, and finally $AlCl_3$ (27.0 g, 202 mmol) in one portion. The mixture was heated to reflux for 1 hour and 80° C. for 16 hours before cooling and addition of 2N HCl (190 ml). The mixture was heated to 80° C. for 30 min, cooled to 20° C., and the pH adjusted to 3–4 with 2N NaOH. The mixture was extracted with $CH_2Cl_2$ with readjustment of the pH to 3–4 after each extraction. The organic extracts were pooled, washed with brine, dried over $Na_2SO_{4(s)}$, filtered and concentrated in vacuo. The residue (28.9 g) was recrystallized from $CHCl_3$/hexanes to afford 26.1 g of pure 2-amino-3,4-dimethyl-α-chloroacetophenone (GC-MS: 197 (M+)). This chloromethylketone (5.02 g, 25.4 mmol) in dioxane (125 mL)/$H_2O$ (15 mL) was treated with $NaBH_4$ (1.06 g, 28 mmol) and heated to reflux for 4 hours. The mixture was concentrated in vacuo and partitioned between $H_2O$/$CH_2Cl$ at pH ~7. The organic extracts were pooled, dried over $MgSO_{4(s)}$, filtered and concentrated in vacuo to afford the crude indole product (2.9 g) which could be reduced directly or sublimed in vacuo to afford 1.55 g of the title compound so pure indole (GC-MS; 145 (M+)).

Preparation 26

6,7,8,9-Tetrahydro-1H-benzo[g]indole

This material was prepared from 5,6,7,8-tetrahydronaphthyl-1-mine via the α-chloroacetophenone intermediate in 76% overall yield utilizing a procedure analogous to that described above for Preparation 25 (GC-MS: 171 (M+)).

Preparation 27

6-Fluoro-7-methylindole

This material was prepared from 3-fluoro-2-methylaniline via its α-chloromethyl ketone derivative in 46% overall yield utilizing a procedure analogous to that described above for Preparation 25 ((GC-MS: 149 (M+)).

Preparation of Substituted Isatins from the Corresponding Anilines and $BH_3$/THF Mediated Reduction of Oxindoles and Isatins to Indoles Preparation 28

1,2,3,5-Tetrahydro-pyrrolo[2,3-f]indole

A solution of 1-acetyl-5-amino-indoline (4.94 g, 28.03 mmol) in conc. HCl (250 mL) and $H_2O$ (17 mL) was added to a mixture of chloral hydrate (5.12 g, 31.0 mmol), and $Na_2SO_4$ (73.8 g, 0.52 mol) in $H_2O$ (68 mL). Once all materials were dissolved, hydroxylamine hydrochloride (6.27 g, 190 mmol) was added and the solution was heated to boiling over 30 minutes and maintained at a boil for 30 minutes. The precipitate which formed upon cooling to 20° C. was removed by filtration, washed with $H_2O$, and dried in vacuo to constant mass to afford 6.68 g. of the 1-acetyl-5-[2-(isonitroso)acetamido]indoline (LC-MS: 248 (MH+)). This material was added in small portions over 30 minutes to conc. $H_2SO_4$ (20 mL) while stirring at 50° C. When the addition was complete the mixture was heated to 80° C. for 10 minutes, cooled to 20° C., and poured into ice/water (300 mL). The precipitate was filtered, washed with $H_2O$ and dried in vacuo to yield 6.02 g of the 1-acetyl isatin derivative (LC-MS: 248 (M+NH4+). A sample (2.68 g, 11.4 mmol) of this product was heated to 50° C. in dioxane (23 mL)/6N HCl (25 mL) for 16 hours. Concentration of the mixture in vacuo at 40° C. yielded the crude deacetyled isatin product (LC-MS: 189 (MH$^+$)) which was redissolved in THF (50 mL) and reduced directly by addition of 1M borane/THF (114 mL, ~10 eq.). After stirring 16 hours at 20° C. the mixture was carefully quenched with H$_2$O (50 mL), diluted with brine, and the pH adjusted to 10–11 before extraction with EtOAc. The organic extracts were pooled, dried over Na$_2$SO$_{4(s)}$, filtered and concentrated in vacuo. The residue was recrystallized from Et$_2$O/hexanes to afford pure 1,2,3,5-tetrahydro-pyrrolo[2,3-f]indole (797 mg, LC-MS: 159 (MH$^+$).

Preparation 29

6-Chloro-5-fluoro-indole

To a solution of 6-chloro-5-fluoro-oxindole (0.49 g, 2.64 mmol) in THF (5 mL) was added slowly 1M BH$_3$ in THF (21.2 mL, 21.2 mmol) over 30 minutes. The mixture was stirred 24 hours and 1N aqueous NaOH (25 mL) was added carefully with stirring. After stirring 20 minutes the mixture was extracted with EtOAc/Et$_2$O (1:1), and the extracts were combined, washed with brine, dried over Na$_2$SO$_{4(s)}$, filtered and concentrated in vacuo to afford 412 mg of the product as a mixture of 6-chloro-5-fluoroindole and 6-chloro-5-fluoroindoline (GC-MS: 169, and 171 (M$^+$), respectively), which was used without further purification.

Preparation 30

5,6-Dichloro-indole

This material was produced in 93% yield from 5,7-dichloro-isatin (1 eq) and BH$_3$/THF (6 mol eq.) utilizing a method analogous to that described for 6-chloro-5-fluoro-indole (Preparation 29).

Preparation 31

6-Chloro-5-nitro-indole

This material was produced from 6-chloro-5-nitro-oxindole (1 eq) and BH$_3$/THF (6 mol eq.) utilizing a method analogous to that described for 6-chloro-5-fluoro-indole (Preparation 29) in 99% yield (contaminated with some 6-chloro-5-nitro-indoline) and used directly in the subsequent borane/pyridine reduction.

Preparation of 5-Hydroxyindoles from Appropriately Substituted Indolines

Preparation 32

5-Hydroxy-6-methyl-indole

Potassium nitrosodisulfonate (1.18 g, 4.4 mmol, 2.2 eq.) in pH 7.0, 0.10M potassium phosphate buffer (80 mL) was added to 6-methyl-indoline (266 mg, 2.0 mmol) in acetone (25 mL) at 20° C. The mixture was stirred for 15 min., and extracted with CHCl$_3$ (4×40 mL). The organic layer was washed with brine, dried over Na$_2$SO$_{4(s)}$, and concentrated in vacuo to afford 290 mg of crude product as purple solid (~80% purity by $^1$H NMR; GC-MS: 147 (M$^+$)) which was used without further purification.

Preparation 33

6-Chloro-5-hydroxy-indole

Chilled potassium nitrosodisulfonate (7.69 g, 28.6 mmol, 2.2 eq.) in pH 7.0, 0.13M potassium phosphate buffer (520 mL) was added to 6-chloroindoline (2.0 g, 13 mmol) in acetone (110 mL) at 0° C. The mixture was stirred at 0° C. for 1 hour and extracted with CHCl$_3$ (250 mL, then 2×75 mL). The organic layer was washed with brine, dried over Na$_2$SO$_{4(s)}$, and concentrated in vacuo to afford 2.34 g of purple solid. This mixture of 6-chloroindoline, 6-chioroindoline, and 6-chloro-5-hydroxyindole was partitioned between degassed aqueous 1N NaOH (150 mL) and ether (3×25 mL). The pH of the aqueous phase was adjusted to ~4 with acetic acid and the desired 6-chloro-5-hydroxy-indole (460 mg; GC-MS: 167 (M$^+$)) was recovered by extraction with CHCl$_3$ and used without further purification.

Preparations 34 & 35

5-Hydroxy-7-methyl-indole and 5-Hydroxy-6,7-dimethyl-indole

These intermediates were prepared from 7-methylindoline and 6,7-dimethylindoline in 73% and 68% yields, respectively, utilizing the procedure described for 5-hydroxy-6-methyl-indole above (Preparation 32).

Brominations of Indolines and Larger Annelated-anilines

Preparation 36

8-Bromo-2,3,4,5-tetrahydro-1H-benzo[b]azepine

To 2,3,4,5-tetrahydro-1H-benzo[b]azepine (410 mg, 2.78 mmol; from Preparation 41) in conc. H$_2$SO$_4$ (5 mL) was added Ag$_2$SO$_4$ (438 mg, 1.41 mmol). The mixture was stirred until the silver sulfate had dissolved and then Br$_{2(l)}$ (145 μL, 2.80 mmol) was added at 0°–5° C. over 15 minutes. The mixture was stirred in the dark and allowed to warm to 20° C. After 4 hours the mixture was poured into ice/H$_2$O (50 mL), the pH was adjusted to 12–14 by the careful addition of 6N KOH with cooling, and then filtered through a pad of Celite. The pad was washed with CH$_3$CN, CHCl$_3$, and Et$_2$O. The aqueous phase was extracted with EtOAc and the organic extracts and washes were combined, dried over MgSO$_{4(s)}$, filtered and concentrated in vacuo to afford 468 mg of a waxy yellow solid. The 6-bromo (48 mg) and 8-bromo isomers (492 mg; GC-MS: 226, 228 (M$^+$)) were separated by flash chromatography on silica (10% EtOAc/hexanes) and/or recrystallization (Et$_2$O/Hexanes).

Alternative Indoline Preparations

Preparation 37

6-Iodo-indoline

To a stirred slurry of 1-acetyl-6-amino-indoline (17.6g, 100 mmol) in H$_2$O (100 mL) was added concentrated H$_2$SO$_4$ (12.5 mL). After stirring 10 minutes the solution was cooled to 0°–5° C. and NaNO$_2$ (6.91 g, 100 mmol) in H$_2$O (25 mL) was added dropwise over 1 hour. A freshly prepared solution of KI (20.04 g, 121 mmol) in 1M H$_2$SO$_4$ (20 mL) was added dropwise to the dark brown solution with stirring at 0°–10° C. The mixture was allowed to warm to 22° C. for ~30 min., and then the solution was heated to 55° C. until no further production of N$_{2(g)}$ was evident. After cooling the pH was adjusted to ~11 and the mixture was extracted with CHCl$_3$ (3×150 mL). Organic extracts were pooled, washed with brine, dried over MgSO$_{4(s)}$, filtered and concentrated in vacuo. The residue containing 1-acetyl-6-iodo-indoline was treated with KOH (14 g, 250 mmol) in refluxing MeOH (170 mL) with THF (30 mL) in an N$_{2(g)}$ atmosphere for 72 hours. After cooling, HOAc (9 g, 150 mmol) was added and the mixture was concentrated in vacuo. The residue was partitioned between CHCl$_3$ (400 mL) and 5% aqueous NaHCO$_3$ (250 mL), and the organic phase was dried over MgSO$_{4(s)}$, filtered, and concentrated in vacuo. The residue was chromatographed on silica in 30% EtOAc/hexanes to afford pure 6-iodo-indoline (8.7 g; GC/MS: RT=1.51 min., M$^+$=245) as tan crystals.

Preparation 38

6-Trimethylsilanylethynyl-indoline

6-Iodo-indoline (499 mg, 2.04 mmol) was added to a mixture of CuI (77.5 mg, 0.407 mmol), Pd(PPh$_3$)$_4$ (113 mg, 0.097 mmol), and trimethylsilylacetylene (0.432 mL 3.06 mmol) in degassed Et$_2$NH (10 mL). The mixture was stirred at reflux under N$_{2(g)}$ for 30 minutes. Solvent was removed in vacuo and the residue was flash chromatographed on silica (25% EtOAc/hexanes) to afford 364 mg of pure 6-trimethylsilanylethynyl-indoline (GC-MS: 215 (M$^+$)).

Preparation 39

6-Chloro-indoline

This material was conveniently prepared on multigram scale from the cyclization of 2,4-dichlorophenethylamine in the presence of Na$_2$CO$_3$(s) (1.2 mol eq), Cu$_2$Cl$_2$ (0.01 mol eq) and 8-hydroxyquinoline (0.012 mol eq) in isoamyl alcohol (1 vol) at 130° C. for 5 hours. After addition of hydrazine (0.0055 vol) and 1 hour reflux, the mixture was filtered, solvent was removed in vacuo (45° C. @ ~10 mm Hg) and 6-chloro-indoline was obtained pure by vacuum distillation (95°–100° C. @ 2 mm Hg)(65–95%).

Preparation 40

DL-Indoline-2-carboxylic Acid Methyl Ester

DL-indoline-2-carboxylic acid (3.169, 19.4 mmol) was suspended in MeCN (50 mL) with stirring and treated with an etheral solution of CH$_2$N$_2$ (~0.5M) until no further evolution of N$_{2(g)}$ resulted on further additions and the yellow color of the reagent persisted. The solution was concentrated in vacuo and the residue was taken up in EtOAc (150 mL), washed with saturated aqueous NaHCO$_3$ (3×50 mL) and brine, dried over MgSO$_{4(s)}$, filtered and concentrated in vacuo to an oil containing >95% pure methyl ester (3.369; GC/MS: 177 (M$^+$)) which was used without further purification.

Larger Annelated-Aniline Systems

Preparation 41

2,3,4,5-Tetrahydro-1H-benzo[b]azepine

To a solution of 2,3,4,5-tetrahydro-1H-1-benzo[b]azepin-2-one (0.776 g, 4.81 mmol) in THF (10 mL) was added 1M BH$_3$ in THF (38.5 ml, 38.5 mmol; 8 eq.) dropwise over 30 minutes at 0° C. The solution was stirred 24 hours at 20° C. and quenched by the dropwise addition of H$_2$O (40 mL). The mixture was diluted with brine and extracted with EtOAc/Et$_2$O (2:1). The organic extracts were washed with 1N NaOH, pooled, dried over MgSO$_{4(s)}$, filtered and concentrated in vacuo to afford 703 mg (~99%) of crude product (GC-MS: 147 (M$^+$)) which was used without further purification.

Preparation 42

1,2,3,4,5,6-Hexahydro-benzo[b]azocine was prepared by the BH$_3$/THF mediated reduction of the 1,2,3,4,5,6-hexahydro-1-benzo[b]azocin-2-one in a manner analogous to that described above for preparation 41.

I claim:
1. A compound of Formula I

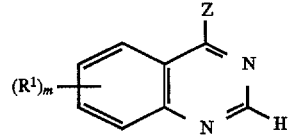

Formula I and the pharmaceutically acceptable salts and stereoisomers thereof wherein Z is

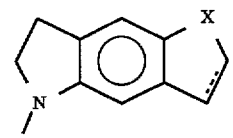

X is —N(H)—;

R$^1$ for each occurrence is substituted independently in the 6 and/or 7 position;

R$^1$ for each occurrence is independently hydroxy, (C$_1$–C$_4$) alkoxy, hydroxy(C$_2$–C$_4$)alkoxy, amino(C$_2$–C$_4$)alkyl, amino(C$_2$–C$_4$)alkoxy, (C$_1$–C$_4$)alkoxy(C$_2$–C$_4$)alkoxy, (C$_1$–C$_4$)alkylenedioxy, hydroxy(C$_1$–C$_4$)alkyl(C$_1$–C$_4$) alkylenedioxy, (C$_1$–C$_4$)alkoxy(C$_1$–C$_4$)alkyl(C$_1$–C$_4$) alkylenedioxy, mono-N- or di-N,N-(C$_1$–C$_4$)alkylamino (C$_2$–C$_4$)alkoxy, 3- or 4-(C$_1$–C$_4$)alkoxy-(2-hydroxy)-(C$_3$–C$_4$)alkoxy, carboxy(C$_1$–C$_4$)alkoxy, morpholino (C$_2$–C$_4$)alkoxy, imidazol-1-yl(C$_2$–C$_4$)alkoxy, 4(C$_1$–C$_4$) alkylpiperazin-1-yl-(C$_2$–C$_4$)alkoxy, (C$_1$–C$_4$)alkoxy (C$_1$–C$_4$)alkanoyloxy, nitro, hydroxylamino, amino, mono-N- or di-N,N-(C$_1$–C$_4$)alkylamino, (C$_1$–C$_4$) alkanoylamino, hydroxy(C$_2$–C$_4$)alkylamino, (C$_1$–C$_4$) alkoxy(C$_2$–C$_4$)alkylamino, (C$_1$–C$_4$)alkylsulfonamido, morpholino, (C$_1$–C$_4$)alkyl-piperazin-1-yl, bis(C$_1$–C$_4$) alkanesulfonamido, di(C$_1$–C$_4$)alkylamino(C$_2$–C$_4$) alkylamino, (C$_1$–C$_4$)alkylamino(C$_2$–C$_4$)alkylamino, imidazol-1-yl, piperidin-1-yl, pyrrolidin-1-yl, (C$_1$–C$_4$) alkoxy(C$_1$–C$_4$)alkylcarbonylamino, N-(C$_1$–C$_4$)alkyl-N-(C$_1$–C$_4$)alkanoyl-amino, carboxy, (C$_1$–C$_4$) alkoxycarbonyl, (C$_1$–C$_4$)alkoxycarbonyl(C$_1$–C$_4$) alkoxy, amido, mono-N- or di-N,N-(C$_1$–C$_4$) alkylaminocarbonyl, mono-N- or di-N,N-(hydroxy (C$_2$–C$_4$)alkyl)aminocarbonyl, (C$_1$–C$_4$)alkyl, hydroxy (C$_1$–C$_4$)alkyl, mono-N- or di-N,N-((C$_1$–C$_4$)alkoxy (C$_1$–C$_4$)alkyl)amino(C$_1$–C$_4$)alkyl, mono-N- or di-N,N-(C$_1$–C$_4$)alkylamino(C$_1$–C$_4$)alkyl, (C$_1$–C$_4$) alkanoylamino(C$_1$–C$_4$)alkyl, (C$_1$–C$_4$)alkoxy(C$_2$–C$_4$) alkoxy(C$_1$–C$_4$)alkyl, (C$_1$–C$_4$)alkylthio, (C$_1$–C$_4$)alkoxy (C$_2$–C$_4$)alkylthio or hydroxy (C$_2$–C$_4$)alkylthio; and m is 0, 1 or 2.

2. A compound of Formula I

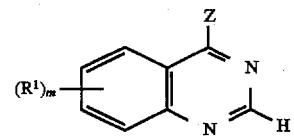

Formula I and the pharmaceutically acceptable salts and stereoisomers thereof wherein Z is

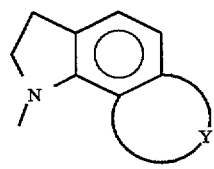

or

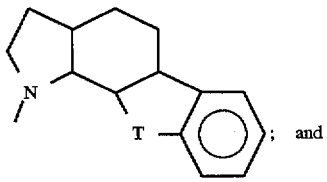

R[1] for each occurrence is independently substituted in the 6 and/or 7 position;

R[1] for each occurrence is independently hydroxy, $(C_1-C_4)$ alkoxy, hydroxy$(C_2-C_4)$alkoxy, amino$(C_2-C_4)$alkyl, amino$(C_2-C_4)$alkoxy, $(C_1-C_4)$alkoxy$(C_2-C_4)$alkoxy, $(C_1-C_4)$alkylenedioxy, hydroxy$(C_1-C_4)$alkyl$(C_1-C_4)$ alkylenedioxy, $(C_1-C_4)$alkoxy$(C_1-C_4)$alkyl$(C_1-C_4)$ alkylenedioxy, mono-N- or di-N,N-$(C_1-C_4)$alkylamino $(C_2-C_4)$alkoxy, 3- or 4-$(C_1-C_4)$alkoxy-(2-hydroxy)- $(C_3-C_4)$alkoxy, carboxy $(C_1-C_4)$alkoxy, morpholino $(C_2-C_4)$alkoxy, imidazol-1-yl$(C_2-C_4)$alkoxy, 4$(C_1-C_4)$ alkylpiperazin-1-yl-$(C_2-C_4)$alkoxy, $(C_1-C_4)$alkoxy $(C_1-C_4)$alkanoyloxy, nitro, hydroxylamino, amino, mono-N- or di-N,N-$(C_1-C_4)$alkylamino, $(C_1-C_4)$ alkanoylamino, hydroxy$(C_2-C_4)$alkylamino, $(C_1-C_4)$ alkoxy$(C_2-C_4)$alkylamino, $(C_1-C_4)$alkylsulfonamido, morpholino, $(C_1-C_4)$alkyl-piperazin-1-yl, bis$(C_1-C_4)$ alkanesulfonamido, di$(C_1-C_4)$alkylamino$(C_2-C_4)$ alkylamino, $(C_1-C_4)$alkylamino$(C_2-C_4)$alkylamino, imidazol-1-yl, piperidin-1-yl, pyrrolidin-1-yl, $(C_1-C_4)$ alkoxy$(C_1-C_4)$alkylcarbonylamino, N-$(C_1-C_4)$alkyl- N-$(C_1-C_4)$alkanoyl-amino, carboxy, $(C_1-C_4)$ alkoxycarbonyl, $(C_1-C_4)$alkoxycarbonyl$(C_1-C_4)$ alkoxy, amido, mono-N- or di-N,N-$(C_1-C_4)$ alkylaminocarbonyl, mono-N- or di-N,N-(hydroxy $(C_2-C_4)$alkyl)aminocarbonyl, $(C_1-C_4)$alkyl, hydroxy $(C_1-C_4)$alkyl, mono-N- or di-N,N-(($(C_1-C_4)$alkoxy $(C_1-C_4)$alkyl)amino$(C_1-C_4)$alkyl, mono-N- or di-N,N- $(C_1-C_4)$alkylamino$(C_1-C_4)$alkyl, $(C_1-C_4)$ alkanoylamino$(C_1-C_4)$alkyl, $(C_1-C_4)$alkoxy$(C_2-C_4)$ alkoxy$(C_1-C_4)$alkyl, $(C_1-C_4)$alkylthio, $(C_1-C_4)$alkoxy $(C_2-C_4)$alkylthio or hydroxy$(C_2-C_4)$alkylthio;

m is 0, 1 or 2;

Y completes a 5 or 6 membered aromatic, or partially saturated ring which may incorporate an oxygen or sulfur atom; and T is methylene, —N(H)—, thio or oxy.

3. A compound of Formula I

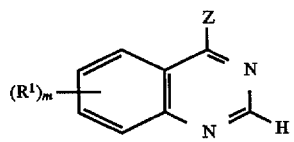

Formula I and the pharmaceutically acceptable salts and stereoisomers thereof wherein Z is

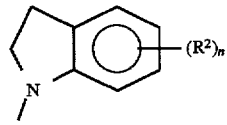

n is 1, 2 or 3;

m is 1 or 2;

R[1] for each occurrence is independently hydroxy, $(C_1-C_4)$ alkoxy, hydroxy$(C_2-C_4)$alkoxy, amino$(C_2-C_4)$alkyl, amino$(C_2-C_4)$alkoxy, $(C_1-C_4)$alkoxy$(C_2-C_4)$alkoxy, $(C_1-C_4)$alkylenedioxy, hydroxy$(C_1-C_4)$alkyl$(C_1-C_4)$ alkylenedioxy, $(C_1-C_4)$alkoxy$(C_1-C_4)$alkyl$(C_1-C_4)$ alkylenedioxy, mono-N- or di-N,N-$(C_1-C_4)$alkylamino $(C_2-C_4)$alkoxy, 3- or 4-$(C_1-C_4)$alkoxy-(2-hydroxy)- $(C_3-C_4)$alkoxy, carboxy $(C_1-C_4)$alkoxy, morpholino $(C_2-C_4)$alkoxy, imidazol-1-yl$(C_2-C_4)$alkoxy, 4$(C_1-C_4)$ alkylpiperazin-1-yl-$(C_2-C_4)$alkoxy, $(C_1-C_4)$alkoxy $(C_1-C_4)$alkanoyloxy, nitro, hydroxylamino, amino, mono-N- or di-N,N-$(C_1-C_4)$alkylamino, $(C_1-C_4)$ alkanoylamino, hydroxy$(C_2-C_4)$alkylamino, $(C_1-C_4)$ alkoxy$(C_2-C_4)$alkylamino, $(C_1-C_4)$alkylsulfonamido, morpholino, $(C_1-C_4)$alkyl-piperazin-1-yl, bis$(C_1-C_4)$ alkanesulfonamido, di$(C_1-C_4)$alkylamino$(C_2-C_4)$ alkylamino, $(C_1-C_4)$alkylamino$(C_2-C_4)$alkylamino, imidazol-1-yl, piperidin-1-yl, pyrrolidin-1-yl, $(C_1-C_4)$ alkoxy$(C_1-C_4)$alkylcarbonylamino, N-$(C_1-C_4)$alkyl- N-$(C_1-C_4)$alkanoyl-amino, carboxy, $(C_1-C_4)$ alkoxycarbonyl, $(C_1-C_4)$alkoxycarbonyl$(C_1-C_4)$ alkoxy, amido, mono-N- or di-N,N-$(C_1-C_4)$ alkylaminocarbonyl, mono-N- or di-N,N-(hydroxy $(C_2-C_4)$alkyl)aminocarbonyl, $(C_1-C_4)$alkyl, hydroxy $(C_1-C_4)$alkyl, mono-N- or di-N,N-(($(C_1-C_4)$alkoxy $(C_1-C_4)$alkyl)amino$(C_1-C_4)$alkyl, mono-N- or di-N,N- $(C_1-C_4)$alkylamino$(C_1-C_4)$alkyl, $(C_1-C_4)$ alkanoylamino$(C_1-C_4)$alkyl, $(C_1-C_4)$alkoxy$(C_2-C_4)$ alkoxy$(C_1-C_4)$alkyl, $(C_1-C_4)$alkylthio, $(C_1-C_4)$alkoxy $(C_2-C_4)$alkylthio or hydroxy$(C_2-C_4)$alkylthio; and R[2] for each occurrence is independently nitro, halo, $(C_1-C_4)$alkyl, pyrrol-1-yl, hydroxyl, amino, mono-N- or di-N,N-$(C_1-C_4)$alkylamino, amino$(C_1-C_4)$alkyl, azido, ethenyl, ethynyl, $(C_1-C_4)$alkylenedioxy, phenyl or $(C_1-C_4)$alkylthio.

4. A compound of Formula I

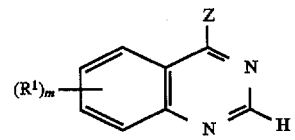

Formula I and the pharmaceutically acceptable salts and stereoisomers thereof wherein Z is

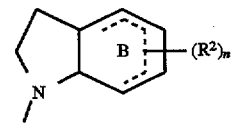

the B six membered ring has 0, 1 or 2 double bonds in the dotted line region;

n is 0–2;

$R^2$ for each occurrence is independently halo, hydroxy or $(C_1-C_4)$alkyl;

m is 0, 1 or 2; and $R^1$ for each occurrence is substituted independently in the 6 and/or 7 positions and is hydroxy, $(C_1-C_4)$alkoxy, hydroxy$(C_2-C_4)$alkoxy, amino$(C_2-C_4)$alkyl, amino$(C_2-C_4)$alkoxy, $(C_1-C_4)$alkoxy$(C_2-C_4)$alkoxy, $(C_1-C_4)$alkylenedioxy, hydroxy$(C_1-C_4)$alkyl$(C_1-C_4)$ alkylenedioxy, $(C_1-C_4)$alkoxy$(C_1-C_4)$alkyl$(C_1-C_4)$ alkylenedioxy, mono-N- or di-N,N-$(C_1-C_4)$alkylamino$(C_2-C_4)$alkoxy, 3- or 4-$(C_1-C_4)$alkoxy-(2-hydroxy)-$(C_3-C_4)$alkoxy, carboxy $(C_1-C_4)$alkoxy, morpholino$(C_2-C_4)$alkoxy, imidazol-1-yl$(C_2-C_4)$alkoxy, 4$(C_1-C_4)$ alkylpiperazin-1-yl-$(C_2-C_4)$alkoxy, $(C_1-C_4)$alkoxy$(C_1-C_4)$alkanoyloxy, nitro, hydroxylamino, amino, mono-N- or di-N,N-$(C_1-C_4)$alkylamino, $(C_1-C_4)$ alkanoylamino, hydroxy$(C_2-C_4)$alkylamino, $(C_1-C_4)$ alkoxy$(C_2-C_4)$alkylamino, $(C_1-C_4)$alkylsulfonamido, morpholino, $(C_1-C_4)$alkyl-piperazin-1-yl, bis$(C_1-C_4)$ alkanesulfonamido, di-N,N-$(C_1-C_4)$alkylamino$(C_2-C_4)$alkylamino, $(C_1-C_4)$alkylamino$(C_2-C_4)$ alkylamino, piperidin-1-yl, imidazol-1-yl, pyrrolidin-1-yl, $(C_1-C_4)$alkoxy$(C_1-C_4)$alkylcarbonylamino, N-$(C_1-C_4)$alkyl-N-$(C_1-C_4)$alkanoyl-amino, carboxy, $(C_1-C_4)$alkoxycarbonyl, $(C_1-C_4)$alkoxycarbonyl$(C_1-C_4)$alkoxy, amido, mono-N- or di-N,N-$(C_1-C_4)$ alkylaminocarbonyl, mono-N- or di-N,N-(hydroxy$(C_2-C_4)$alkyl)aminocarbonyl, $(C_1-C_4)$alkyl, hydroxy$(C_1-C_4)$alkyl, mono-N- or di-N,N-($(C_1-C_4)$alkoxy$(C_1-C_4)$alkyl)amino$(C_1-C_4)$alkyl, mono-N- or di-N,N-$(C_1-C_4)$alkylamino$(C_1-C_4)$alkyl, $(C_1-C_4)$ alkanoylamino$(C_1-C_4)$alkyl, $(C_1-C_4)$alkoxy$(C_2-C_4)$ alkoxy$(C_1-C_4)$alkyl, $(C_1-C_4)$alkylthio, $(C_1-C_4)$alkoxy$(C_2-C_4)$alkylthio or hydroxy$(C_2-C_4)$alkylthio.

5. A method of treating a noncancerous hyperproliferative disorder which comprises administering to a mammal in need of such treatment a noncancerous hyperproliferative disorder treating amount of a compound of claim 1, 2, 3 or 4.

6. A compound according to claim 3 wherein $R^2$ for each occurrence is independently halo, nitro, hydroxy or methyl;

$R^1$ is $(C_1-C_4)$alkoxy or $(C_1-C_4)$alkyl;

m is 2; and n is 1 or 2.

7. The compound as recited in claim 3 wherein m is 2;

$R^1$ is 6-methoxy;

$R^1$ is 7-methoxy;

n is 2;

$R^2$ is 5-fluoro; and $R^2$ is 6-bromo.

8. The compound as recited in claim 3 wherein m is 2;

$R^1$ is 6-(2-methoxyethoxy);

$R^1$ is 7-(2-methoxyethoxy);

n is 1; and $R^2$ is 6-chloro.

9. The compound as recited in claim 3 wherein m is 2;

$R^1$ is 6-methoxy;

$R^1$ is 7-(2-hydroxyethoxy);

n is 1; and $R^2$ is 6-chloro.

10. The compound as recited in claim 3 wherein m is 1;

$R^1$ is 6-amino;

n is 1; and $R^2$ is 6-chloro.

11. The compound as recited in claim 3 wherein m is 2;

$R^1$ is 6-methoxy;

$R^1$ is 7-(3-hydroxypropoxy);

n is 1; and $R^2$ is 6-chloro.

12. The compound as recited in claim 3 wherein m is 2;

$R^1$ is 7-(2-imidazol-1-yl-ethoxy);

$R^1$ is 6-methoxy;

n is 1; and $R^2$ is 6-chloro.

13. The compound as recited in claim 3 wherein m is 2;

$R^1$ is 6-methoxy;

$R^1$ is 7-methoxy;

n is 1; and $R^2$ is 5-amino.

14. The compound as recited in claim 3 wherein m is 2;

$R^1$ is 6-methoxy;

$R^1$ is 7-(2-methoxy-ethoxy);

n is 2;

$R^2$ is 5-fluoro; and $R^2$ is 6-bromo.

15. The compound as recited in claim 3 wherein m is 2;

$R^1$ is 6-methoxy;

$R^1$ is 7-methoxy;

n is 2;

$R^2$ is 5-amino; and $R^2$ is 6-chloro.

16. The compound as recited in claim 3 wherein m is 2;

$R^1$ is 6-methoxy;

$R^1$ is 7-(2-hydroxy-3-methoxy)propoxy;

n is 1; and $R^2$ is 6-chloro.

17. A method of treating cancer which comprises administering to a mammal in need of such treatment a cancer treating amount of a compound of claim 1, 2, 3 or 4.

18. A method as recited in claim 17 wherein the disease is brain, lung, squamous cell, bladder, gastric, pancreatic, hepatic, renal, colorectal, breast, head, neck, oesophageal, gynecological or thyroid cancer.

19. A method as recited in claim 5 wherein the noncancerous hyperproliferative disorder is psoriasis or benign prostatic hyperplasia.

20. A pharmaceutical composition for the treatment of a hyperproliferative disorder in a mammal which comprises a hyperproliferative disease treating amount of a compound of claim 1, 2, 3 or 4 and a pharmaceutically acceptable carrier.

* * * * *